(12) United States Patent  (10) Patent No.: US 8,715,343 B2
Navia et al.  (45) Date of Patent: May 6, 2014

(54) APPARATUS AND METHOD FOR DELIVERING AN IMPLANTABLE MEDICAL DEVICE TO A DISEASED CARDIAC VALVE

(75) Inventors: Jose L. Navia, Shaker Heights, OH (US); Ji-Feng Chen, Lakewood, OH (US); Shengqiang Gao, Beachwood, OH (US); Brian L. Davis, Moreland Hills, OH (US); David J. Horvath, Euclid, OH (US)

(73) Assignee: The Cleveland Clinic Foundation, Cleveland, OH (US)

( * ) Notice: Subject to any disclaimer, the term of this patent is extended or adjusted under 35 U.S.C. 154(b) by 73 days.

(21) Appl. No.: 13/394,853

(22) PCT Filed: Sep. 8, 2010

(86) PCT No.: PCT/US2010/048094
§ 371 (c)(1),
(2), (4) Date: Mar. 8, 2012

(87) PCT Pub. No.: WO2011/031733
PCT Pub. Date: Mar. 17, 2011

(65) Prior Publication Data
US 2012/0203332 A1  Aug. 9, 2012

Related U.S. Application Data

(60) Provisional application No. 61/240,777, filed on Sep. 9, 2009.

(51) Int. Cl.
*A61F 2/24* (2006.01)

(52) U.S. Cl.
USPC ......................................................... 623/2.11

(58) Field of Classification Search
USPC ........... 623/1.11, 1.12, 1.23, 2.11, 2.36–2.41;
227/175.1–182.1
See application file for complete search history.

(56) References Cited

U.S. PATENT DOCUMENTS

| 2003/0078671 A1 | 4/2003 | Lesniak et al. |
| 2007/0225681 A1 | 9/2007 | House |
| 2008/0039881 A1* | 2/2008 | Greenberg ..................... 606/170 |
| 2009/0024043 A1 | 1/2009 | MacLeod et al. |
| 2009/0143766 A1 | 6/2009 | Calabro et al. |

\* cited by examiner

*Primary Examiner* — Ryan Severson
*Assistant Examiner* — Katherine M Shi
(74) *Attorney, Agent, or Firm* — Tarolli, Sundheim, Covell & Tummino LLP

(57) ABSTRACT

An apparatus is provided for delivering an implantable medical device to a diseased cardiac valve includes an elongated shank, a brace member, and a locking mechanism. The shank has a first end portion, a second end portion, and a first longitudinal axis extending between the end portions. The first end portion includes a rotatable annular lower support and a fixing member. The lower support includes an annular ring having oppositely disposed upper and lower surfaces and a plane extending radially between the upper and lower surfaces. The brace member includes a barrel portion operably connected to a drive system. The barrel portion includes a first end portion, a second end portion, and a second longitudinal axis extending between the end portions. The drive system includes a housing operably connected to an actuating handle. The locking mechanism is operably connected to the housing and the elongated shank.

11 Claims, 31 Drawing Sheets

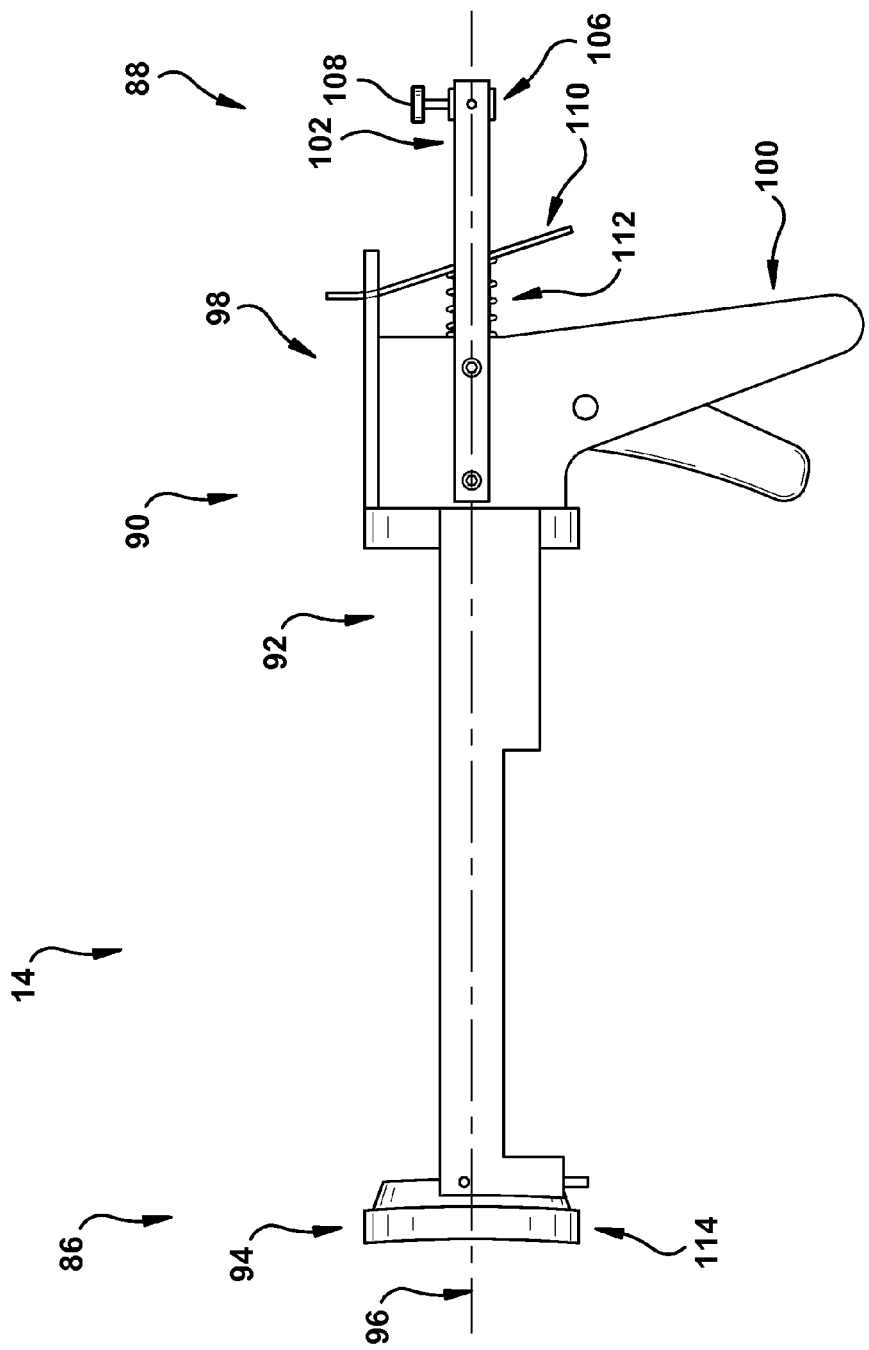

APPARATUS AND METHOD FOR DELIVERING AN IMPLANTABLE MEDICAL DEVICE TO A DISEASED CARDIAC VALVE

RELATED APPLICATION

This application claims priority from U.S. Provisional Application No. 61/240,777, filed Sep. 9, 2009, the subject matter of which is incorporated herein by reference.

TECHNICAL FIELD

The present invention relates generally to cardiac valve repair and replacement, and more particularly to an apparatus and method for delivering an implantable medical device to a diseased cardiac valve.

BACKGROUND OF THE INVENTION

Diseased mitral and tricuspid valves frequently need replacement or repair. The mitral and tricuspid valve leaflets or supporting chordae may degenerate and weaken or the annulus may dilate leading to valve leak (i.e., valve insufficiency). The leaflets and chords may become calcified and thickened, rendering them stenotic and obstructing forward blood flow. Finally, each of the valves relies on insertion of the chordae inside the ventricle. If the corresponding ventricle changes shape, the valve support may become non-functional and the valve may leak.

Mitral and tricuspid valve replacement and repair are traditionally performed with a suture technique. During valve replacement, sutures are spaced around the annulus and then attached to a prosthetic valve. The valve is lowered into position and, when the sutures are tied, the valve is fastened to the annulus. The surgeon may remove all or part of the valve leaflets before inserting the prosthetic valve.

In valve repair, a diseased valve is left in situ and surgical procedures are performed to restore its function. Frequently, an annuloplasty ring is used to reduce the size of the annulus. The ring serves to reduce the diameter of the annulus and allow the leaflets to oppose each other normally. Sutures are used to attach a prosthetic ring to the annulus and to assist in plicating the annulus.

In general, the annuloplasty rings and replacement valves must be sutured to the valve annulus during a time consuming and tedious procedure. If the ring is severely malpositioned, then the stitches must be removed and the ring repositioned relative to the valve annulus. In other cases, a less than optimum annuloplasty may be tolerated by the surgeon rather than lengthening the time of the surgery to re-stitch the ring. Moreover, during heart surgery, a premium is placed on reducing the amount of time used to replace and repair valves as the heart is frequently arrested and without perfusion.

SUMMARY OF THE INVENTION

According to one aspect of the present invention, an apparatus is provided for delivering an implantable medical device to a diseased cardiac valve having an inferior aspect and a superior aspect. The apparatus comprises an elongated shank, a brace member, and a locking mechanism. The elongated shank has a first end portion, a second end portion, and a first longitudinal axis extending between the first and second end portions. The first end portion includes a rotatable annular lower support for contacting the inferior aspect of the diseased cardiac valve and a fixing member for securing the implantable medical device to, or in place of, the diseased cardiac valve. The lower support comprises an annular ring having oppositely disposed upper and lower surfaces and a plane extending radially between the upper and lower surfaces. The lower support and the fixing member are movable relative to one another along the first longitudinal axis. The brace member comprises a barrel portion operably connected to a drive system. The barrel portion includes a first end portion, a second end portion, and a second longitudinal axis extending between the first and second end portions. The drive system comprises a housing operably connected to an actuating handle. The drive system is for slidably extending and withdrawing the elongated shank along the second longitudinal axis. The locking mechanism is operably connected to the housing and the elongated shank. The locking mechanism is for securing the lower support and the fixing member at separate points along the first longitudinal axis of said elongated shank.

According to another aspect of the present invention, a method is provided for delivering an implantable medical device to a diseased cardiac valve having an inferior aspect and a superior aspect. One step of the method includes providing an apparatus comprising an elongated shank, a brace member, and a locking mechanism. The elongated shank has a first end portion, a second end portion, and a first longitudinal axis extending between the first and second end portions. The first end portion includes a rotatable annular lower support and a fixing member. The lower support comprises an annular ring having oppositely disposed upper and lower surfaces and a plane extending radially between the upper and lower surfaces. The brace member comprises a barrel portion operably connected to a drive system. The barrel portion includes a first end portion, a second end portion, and a second longitudinal axis extending between the first and second end portions. The drive system comprises a housing operably connected to an actuating handle. The locking mechanism is operably connected to the housing and the elongated shank. The first end portion of the barrel portion is positioned about the superior aspect of the diseased cardiac valve. Next, the lower support is extended through the diseased cardiac valve. At least a portion of the diseased cardiac valve is then sandwiched between the upper and lower supports. After sandwiching the at least a portion of the diseased cardiac valve, the implantable medical device is implanted on, or in place of, the diseased cardiac valve.

According to another aspect of the present invention, an apparatus is provided for delivering an implantable medical device to a diseased cardiac valve having an inferior aspect and a superior aspect. The apparatus comprises an elongated shank, an actuating handle, and a drive system. The elongated shank has a first end portion, a second end portion, and a first longitudinal axis extending between the first and second end portions. The first end portion includes an expandable lower support for contacting the inferior aspect of the diseased cardiac valve and an upper support for securing the implantable medical device to, or in place of, the diseased cardiac valve. The lower support comprises at least two opposable fingers. Each of the fingers has oppositely disposed upper and lower surfaces and a plane that extends radially between the upper and lower surfaces. The upper and lower supports are movable relative to one another along the first longitudinal axis. The actuating handle is operatively connected to the second end portion of the elongated shank. The drive system extends between the lower support and the actuating handle. The drive system is for selectively moving the lower support between an expanded configuration and a collapsed configuration. The radial plane of the lower support extends substantially perpendicular to the first longitudinal axis in the expanded configuration and substantially parallel to the first longitudinal axis in the collapsed configuration.

According to another aspect of the present invention, a method is provided for delivering an implantable medical device to a diseased cardiac valve having an inferior aspect and a superior aspect. One step of the method includes providing an apparatus comprising an elongated shank, an actuating handle, and a drive system. The elongated shank includes a first end portion, a second end portion, and a longitudinal axis extending between the first and second end portions. The first end portion includes an expandable lower support and an upper support. The upper and lower supports are movable relative to one another. The first end portion of the elongated shank is positioned about the superior aspect of the diseased cardiac valve. Next, the lower support is extended through the diseased cardiac valve. At least a portion of the diseased cardiac valve is then sandwiched between the upper and lower supports. After sandwiching the at least a portion of the diseased cardiac valve, the implantable medical device is implanted on, or in place of, the diseased cardiac valve.

BRIEF DESCRIPTION OF THE DRAWINGS

The foregoing and other features of the present invention will become apparent to those skilled in the art to which the present invention relates upon reading the following description with reference to the accompanying drawings, in which:

FIG. 6 is a side view of the brace member in FIG. 1A;

FIG. 25A is an exploded side view showing a drive system being used to expand the lower support shown in FIG. 24A and FIG. 24C;

FIG. 25B is an exploded side view showing the drive system in FIG. 25A being used to collapse the lower support in FIG. 24B and FIG. 24D;

DETAILED DESCRIPTION

Figure 1A:
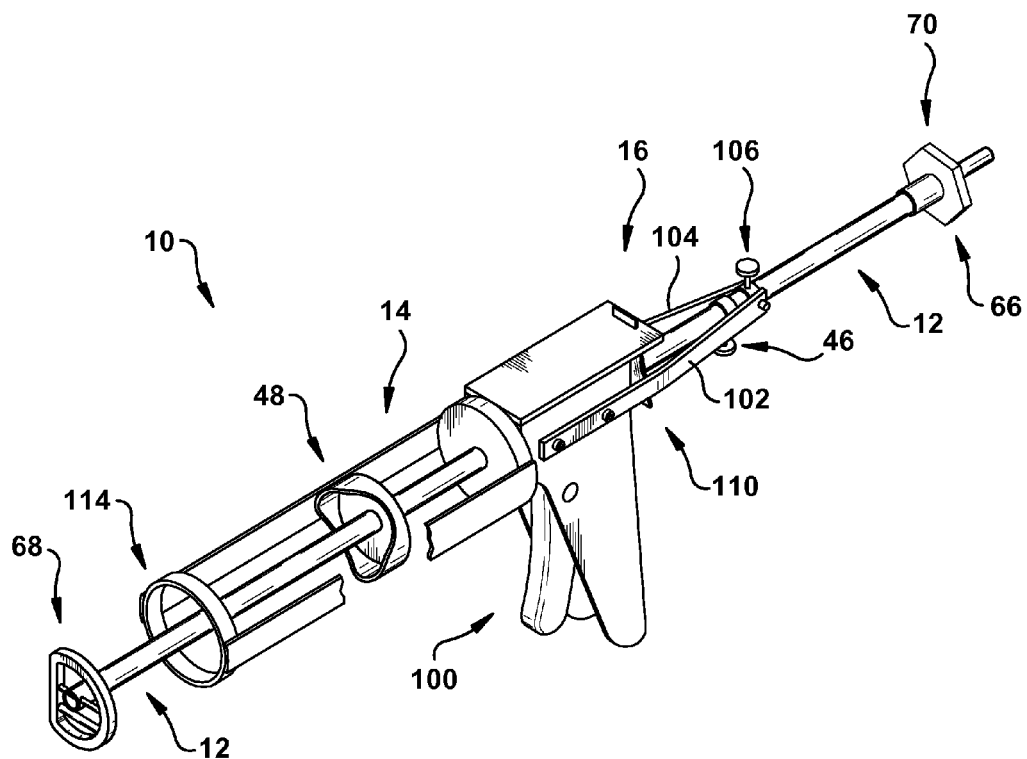
FIG. 1A is a perspective view of an apparatus for delivering an implantable medical device to a diseased cardiac valve constructed according to one aspect of the present invention, the apparatus comprising an elongated shank, a brace member, and a locking mechanism.
Figure 1B:
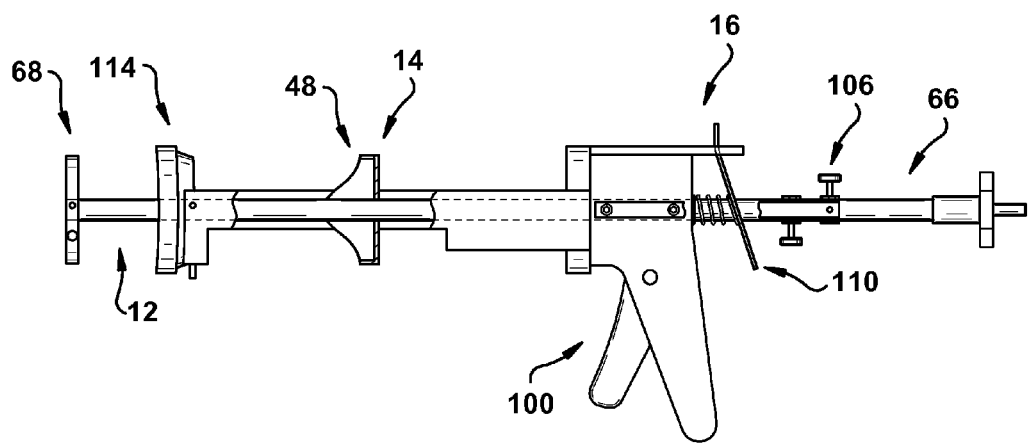
FIG. 1B is a side view of the apparatus in FIG. 1A.

The present invention relates generally to cardiac valve repair and replacement, and more particularly to an apparatus and method for delivering an implantable medical device to a diseased cardiac valve. As representative of one aspect of the present invention, FIGS. 1A-B illustrate an apparatus 10 comprising an elongated shank 12, a brace member 14, and a locking mechanism 16. As described in more detail below, the apparatus 10 facilitates heart stabilization during delivery of an implantable medical device 18 (FIG. 12) to a diseased cardiac valve 20. Although the apparatus 10 (FIGS. 1A-B) is described below for replacing a diseased mitral valve 22 (FIG. 12), it should be understood that the apparatus (FIGS. 1A-B) could also be used to replace other diseased cardiac valves, such as the tricuspid valve (not shown), the pulmonary valve (not shown), and the aortic valve (not shown).

Figure 2:
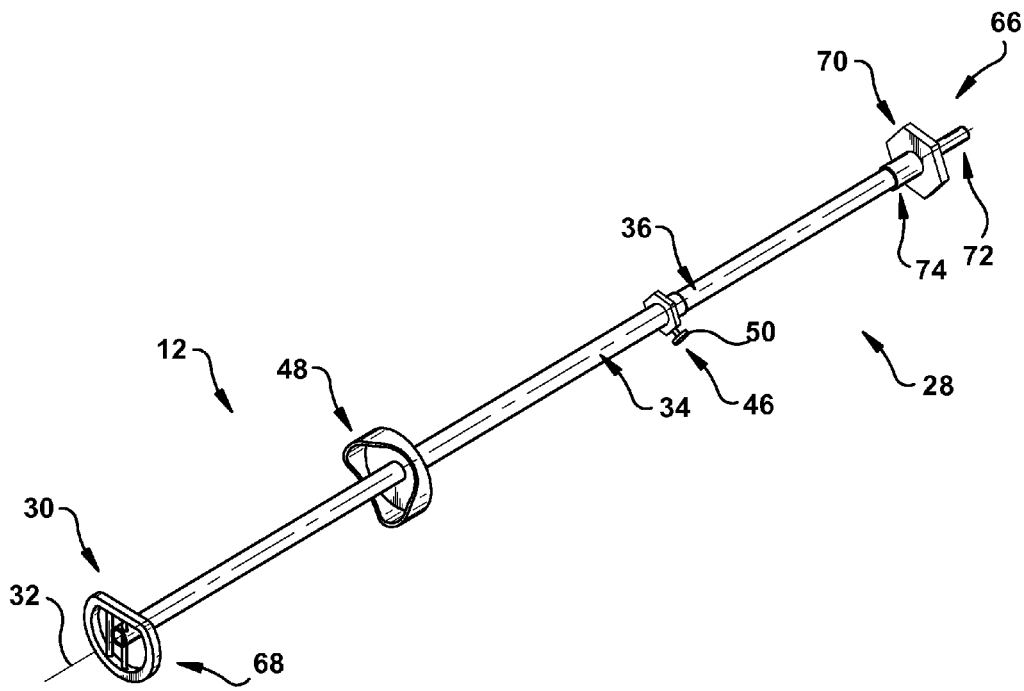
FIG. 2 is a perspective view of the elongated shank in FIGS. 1A-B.

As shown in FIGS. 1A-B, one aspect of the present invention includes an apparatus 10 for delivering an implantable medical device 18 (FIG. 12), such as an annuloplasty ring or a prosthetic valve (not shown) to a diseased cardiac valve 20 having an inferior aspect 24 and a superior aspect 26. The apparatus 10 (FIGS. 1A-B) comprises an elongated shank 12, a brace member 14, and a locking mechanism 16. As shown in FIG. 2, the elongated shank 12 comprises a first end portion 28, a second end portion 30, and a first longitudinal axis 32 extending between the first and second end portions.

Figure 3:
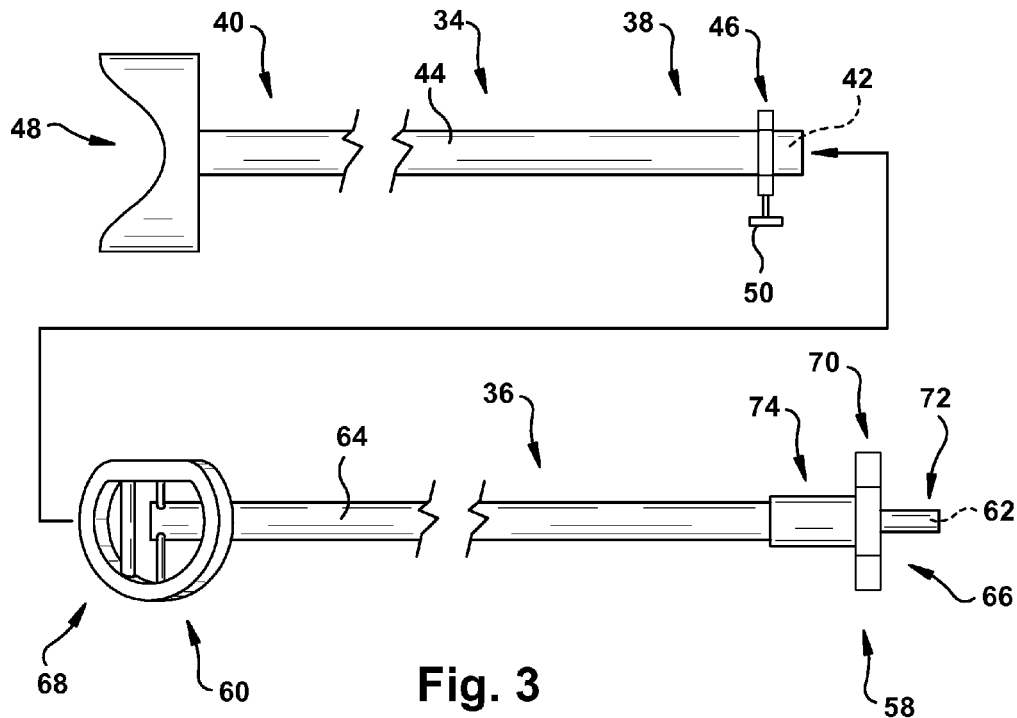
FIG. 3 is a side view of the elongated shank shown in FIG. 2 in an exploded configuration.

The elongated shank 12 is formed from first and second elongated sleeves 34 and 36 (FIG. 3). The first elongated sleeve 34 includes oppositely disposed first and second ends 38 and 40 and a channel 42 extending between the first and second ends. The channel 42 of the first elongated sleeve 34 is defined by an outer surface 44 oppositely disposed from an inner surface (not shown). Additionally, the channel 42 of the first elongated sleeve 34 is adapted to receive the second elongated sleeve 36 as shown in FIG. 3. All or only a portion of the first elongated sleeve 34 can be made of a rigid material, such as a metal or metal alloy.

The first and second ends 38 and 40 of the first elongated sleeve 34 respectively include a first locking member 46 and a fixing member 48. The first locking member 46 has a ring-shaped or bolt-like configuration. As shown in FIG. 3, for example, the first locking member 46 has a hexagonal configuration; however, it will be appreciated that the first locking member can have any desired geometry. The first locking member 46 is securely attached to the outer surface 44 of the first elongated sleeve 34 via a first adjustment screw 50. The first adjustment screw 50 extends through the first locking member 46 into contact with the outer surface 44 of the first elongated sleeve 34. It will be appreciated that more than one adjustment screw 50 can be used to secure the first locking member 46 to the first elongated sleeve 34. The first locking member 46 can be made from a rigid material, such as a metal or metal alloy.

Figure 4A:
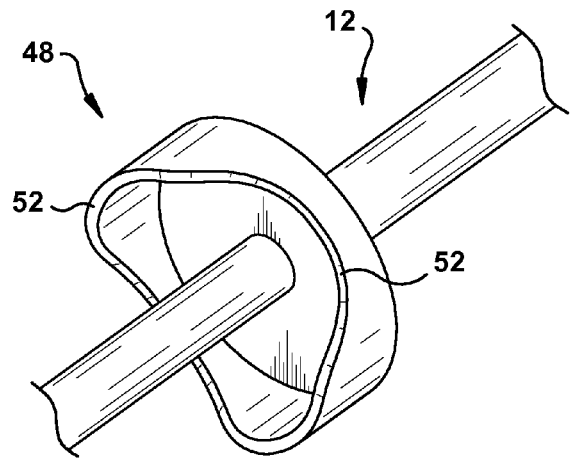
FIG. 4A is a perspective view of a fixing member mounted to the elongated shank in FIG. 2.
Figure 4B:
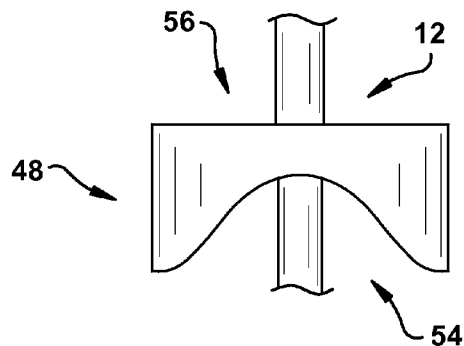
FIG. 4B is a top view of the fixing member in FIG. 4A.
Figure 4C:
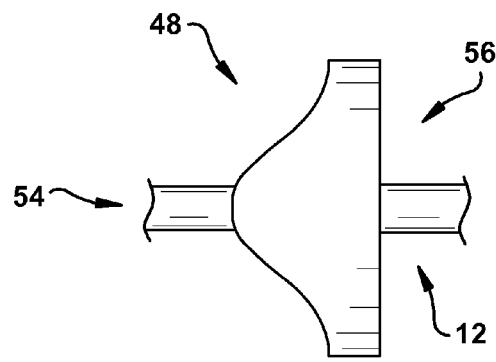
FIG. 4C is a side view of the fixing member in FIG. 4A.

As shown in FIGS. 4A-C, the fixing member 48 has an annular configuration and includes a mating surface 52 that extends circumferentially about a distal end portion 54 that is oppositely disposed from a proximal end portion 56. As shown in FIG. 4A, the proximal end portion 56 of the fixing member 48 includes an aperture (not shown in detail) for receiving the elongated shank 12. The fixing member 48 can be formed from a rigid material, such as a hardened plastic, metal, metal alloy, or a combination thereof.

Referring again to FIG. 3, the second elongated sleeve 36 comprising the elongated shank 12 includes oppositely disposed first and second ends 58 and 60 and a channel 62 extending between the first and second ends. The channel 62 of the second elongated sleeve 36 is defined by an outer surface 64 oppositely disposed from an inner surface (not shown). All or only a portion of the second elongated sleeve 36 can be made of a rigid material, such as a metal or metal alloy.

The first and second ends 58 and 60 of the second elongated sleeve 36 respectively include a lower support adjustment mechanism 66 and a rotatable annular lower support 68. The lower support adjustment mechanism 66 comprises a ring-shaped adjustment member 70 located between first and second adaptive end portions 72 and 74. The first adaptive end portion 72 is securely mated with the adjustment member 70 and extends through the adjustment member into the channel 62 of the second elongated sleeve 36. The second adaptive end portion 74 has a ribbed outer surface (not shown in detail) and is integrally formed with the adjustment member 70. The first end 58 of the second elongated sleeve 36 is slidably mated with the second adaptive end portion 74. As described in more detail below, an axial force (e.g., using tactile means) can be applied to the lower support adjustment mechanism 66, and in particular the adjustment member 70, to rotate the lower support 68.

Figure 5A:
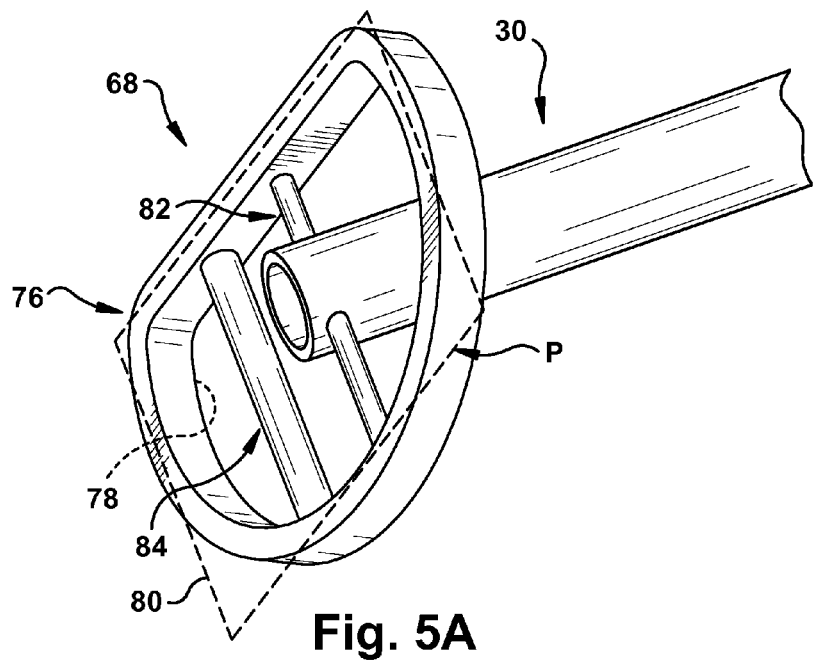
FIG. 5A is an exploded perspective view showing a rotatable annular lower support of the elongated shank (FIG. 2) in a non-deployed configuration.
Figure 5B:
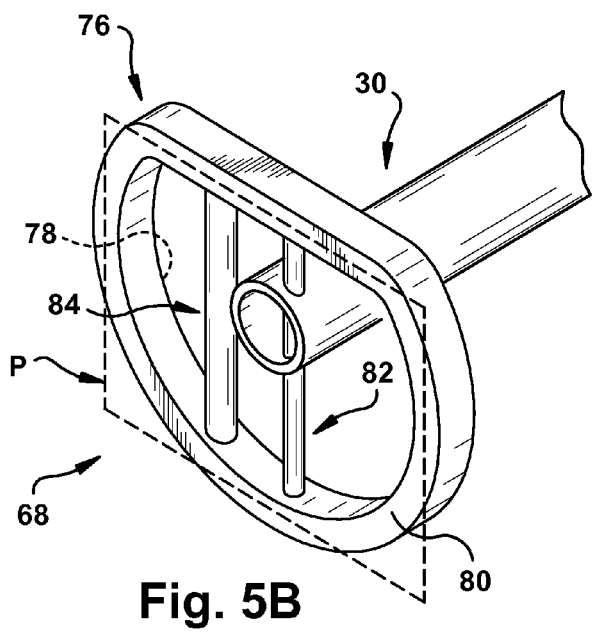
FIG. 5B is an exploded perspective view showing the rotatable annular lower support in FIG. 5A in a deployed configuration.

FIGS. 5A and 5B respectively illustrate the lower support 68 in non-deployed and deployed configurations. The lower support 68 comprises an annular ring 76 having oppositely disposed upper and lower surfaces 78 and 80 and a plane P extending radially between the upper and lower surfaces. All or only a portion of the lower support 68 can have a solid, semi-solid, or porous construction. Additionally, all or only a portion of the lower support 68 can be made of a rigid material, such as a hardened plastic, metal, metal alloy, or a combination thereof. As described in more detail below, the lower support 68 and the fixing member 48 (FIG. 2) are movable relative to one another along the first longitudinal axis 32.

The lower support 68 (FIGS. 5A-B) also includes at least one axle member 82 extending radially between the upper and lower surfaces 78 and 80. The at least one axle member 82 is mated with the second end 60 of the second elongated sleeve 36. Although not shown in detail, the at least one axle member 82 is operably connected to an actuating mechanism that extends between the axle member and the lower support adjustment mechanism 66. As described in greater detail below, the lower support adjustment mechanism 66 can be operated so that the lower support 68 moves between the non-deployed configuration and the deployed configuration.

The lower support 68 additionally includes a strut member 84 extending radially between the upper and lower surfaces 78 and 80. The strut member 84 can be integrally formed with the annular ring 76 and be made from the same or different material as the annular ring and/or the at least one axle member 82. Although the lower support 68 is shown with only one strut member 84 in FIGS. 5A-B, it will be appreciated that the lower support can include a fewer or greater number of strut members.

As shown in FIG. 6, the brace member 14 has an L-shaped configuration and comprises a first end portion 86, a second end portion 88, and a middle portion 90 extending between the end portions. The first end portion 86 has a semi-cylindrical or barrel-shaped configuration and includes oppositely disposed proximal and distal ends 92 and 94. A second longitudinal axis 96 extends between the first and second end portions 86 and 88 of the brace member 14. All or only a portion of the brace member 14 can be made of a rigid material, such as a metal or metal alloy.

The middle portion 90 of the brace member 14 comprises a drive system for moving the elongated shank 12 along the second longitudinal axis 96. The drive system includes a housing 98 operably connected to an actuating handle 100. The housing 98 includes a first support beam 102 and a second support beam 104 (FIG. 1A), each of which is securely connected to a second locking member 106 (FIG. 6).

The second locking member 106 has a hexagonal, ring-like configuration and includes a second adjustment screw 108. The second adjustment screw 108 extends through the body of the second locking member 106 into contact with the outer surface 44 of the first elongated sleeve 34. The second adjustment screw 108 can be rotated in a clockwise or counter-clockwise motion to lock or release the first elongated sleeve 34 (respectively).

The housing 98 additionally includes a lever member 110 operably connected to the first elongated sleeve 34. A portion of the lever member 110 is also operably connected to a spring 112 that extends around the elongated shank 12 between the housing 98 and the lever member. As described in more detail below, the actuating handle 100 is operated in tandem with the lever member 110 to adjust the position the lower support 68 and the fixing member 48. As also described in greater detail below, the first and second support beams 102 and 104, the lever member 110, and the second locking member 106 comprise the locking mechanism 16, which is for securing the lower support 68 and the fixing member 48 at separate points along the first longitudinal axis 32 of the elongated shank 12.

Figure 7A:
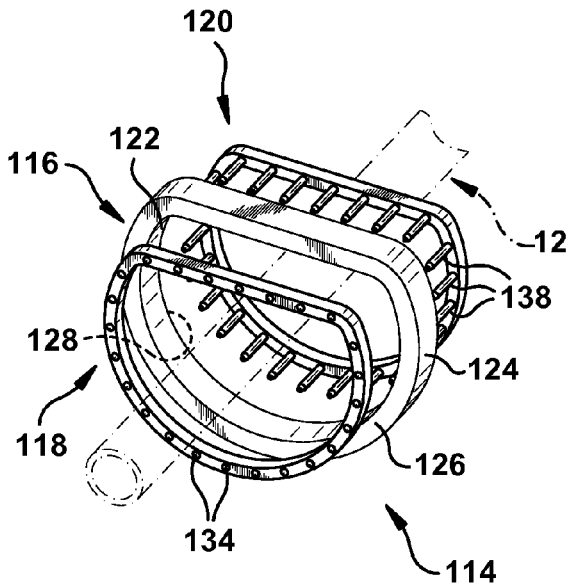
FIG. 7A is an exploded perspective view showing an annular upper support of the brace member in FIG. 1A.
Figure 7B:
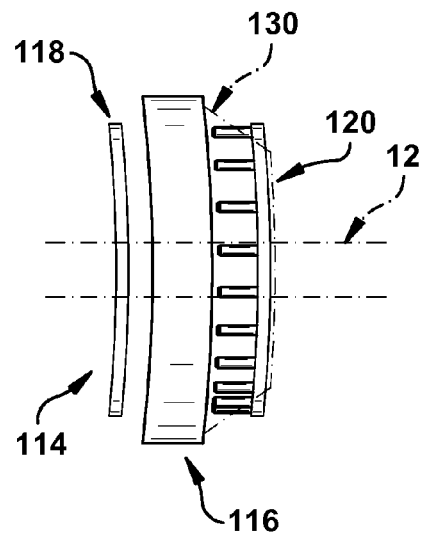
FIG. 7B is an exploded side view of the upper support in FIG. 7A.
Figure 7E:
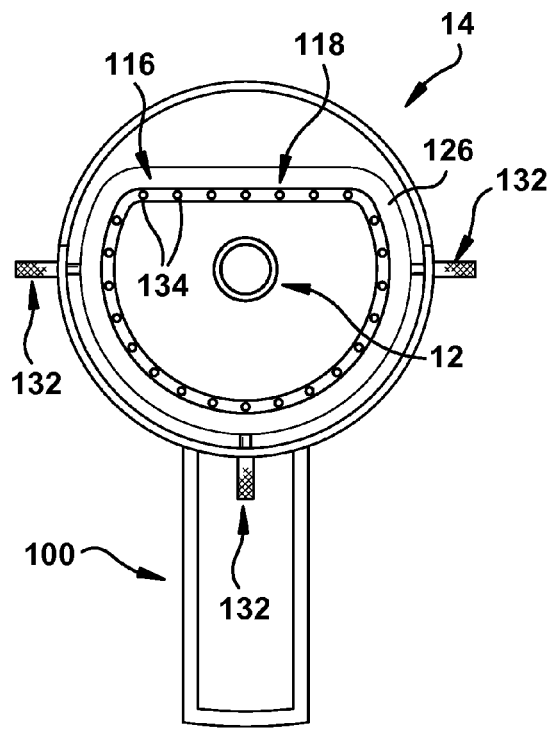
FIG. 7E is a front view of the upper support in FIG. 7B affixed to the brace member (FIG. 1A) (the lower support is not shown for clarity)
Figure 7F:
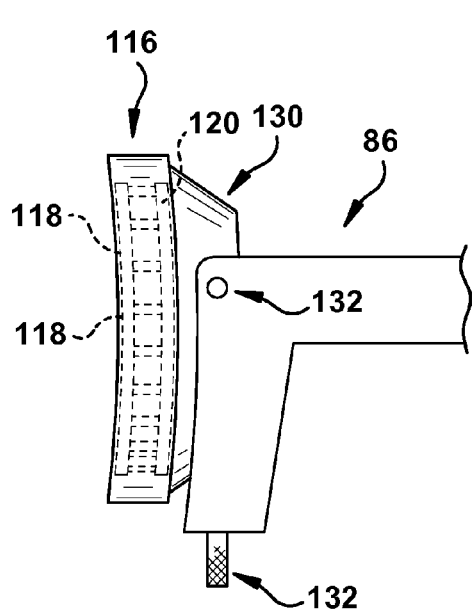
FIG. 7F is an exploded side view showing the upper support affixed to the first end portion of the brace member in FIG. 7E.
Figure 7C:
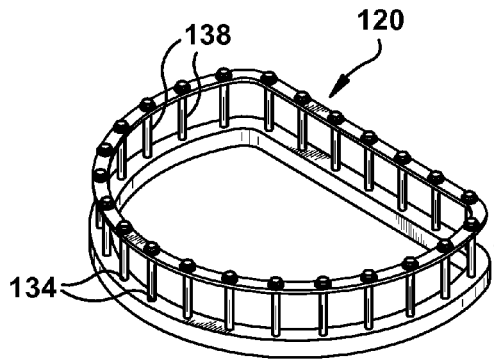
FIG. 7C is a perspective view showing the upper support in FIG. 7B comprising a washer member mated with a penetrating member having a plurality of spikes in a non-deployed configuration.
Figure 7D:
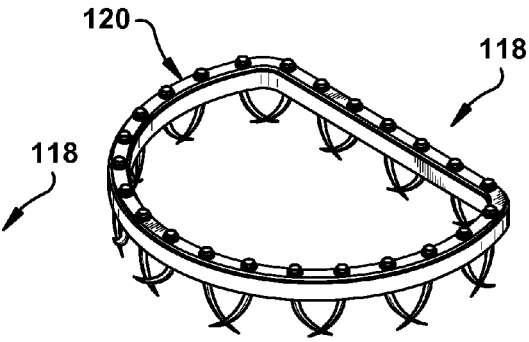
FIG. 7D is a perspective view showing the washer member and the penetrating member in FIG. 7C in a deployed configuration.
Figure 12:
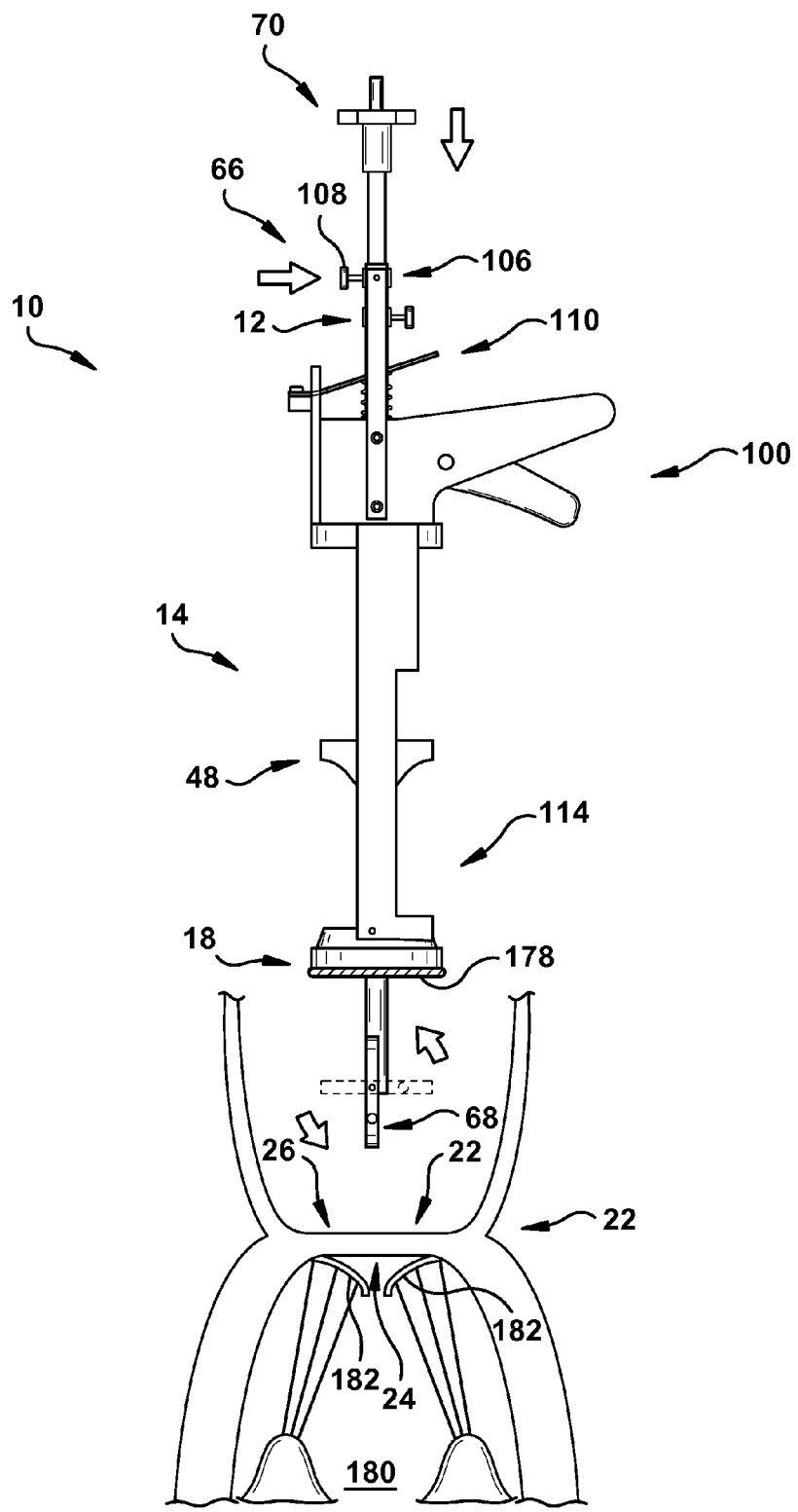
FIG. 12 is a side view of the apparatus in FIGS. 1A-B loaded with an annuloplasty ring and positioned about a diseased mitral valve.

The distal end 94 of the brace member 14 includes an annular upper support 114 (FIGS. 7A-F) for receiving the implantable medical device 18 (FIG. 12). The upper support 114 (FIGS. 7A-F) comprises a main annular member 116, an annular washer member 118, and an annular penetrating member 120. The main annular member 116 (FIGS. 7A-B) includes oppositely disposed inner and outer surfaces 122 and 124, as well as a lower surface 126 oppositely disposed from an upper surface 128. The upper surface 128 additionally includes a thin, annular skirt member 130 integrally formed therewith. The main annular member 116 is securely connected to the distal end 94 of the brace member 14 via a plurality of screws 132 (FIGS. 7E-F). The main annular member 116 can be made of a rigid or semi-rigid material, such as a hardened plastic.

As shown in FIGS. 7A-D, the washer member 118 is securely disposed on the inner surface 122 of the main annular member 116. As described in more detail below, the washer member 118 includes a plurality of pores 134 for receiving the penetrating member 120 and for facilitating deployment of the implantable medical device 18 (FIG. 12). The washer member 118 (FIGS. 7A-D) can be secured to the main annular member 116 using sutures (not shown), for example, or by any other suitable means known in the art, such as pins, clips, magnets, or the like. The washer member 118 can be made of a rigid or semi-rigid material, such as a Nitinol, hardened plastic, or rubber.

The penetrating member 120 comprises a relatively thin, annular base 136 and a plurality of spikes 138 extending radially from the annular base. In a non-deployed configuration of the penetrating member 120 (FIG. 7C), a distal tip (not shown in detail) of each of the spikes 138 partially extends into a corresponding pore 134 of the washer member 118 so that the penetrating member is secured about the washer member. The penetrating member 120 can include any number of spikes 138 such that the penetrating member can mate with the washer member 118. The penetrating member 120 can be comprised of a rigid or semi-rigid material, such as a metal or metal alloy (e.g., stainless steel or aluminum). As described in greater detail below, the fixing member 48 can be contacted with the penetrating member 120 to drive the spikes 138 into the pores 134 of the washer member 118 (FIG. 7D), through the implantable medical device 18 (FIG. 12), and into the tissue surrounding the diseased cardiac valve 20.

Figure 7G:
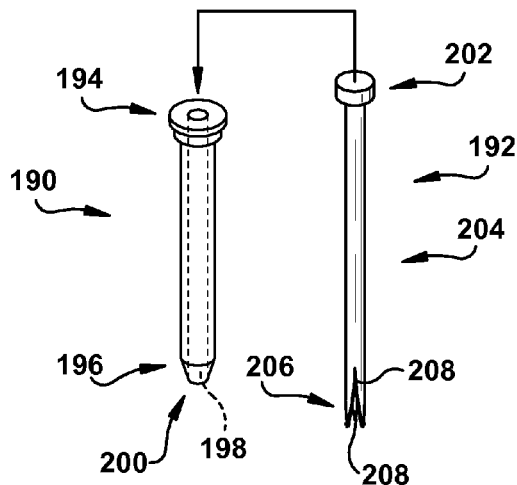
FIG. 7G is an exploded perspective view showing an alternative configuration of the spikes shown in FIG. 7C.
Figure 7H:
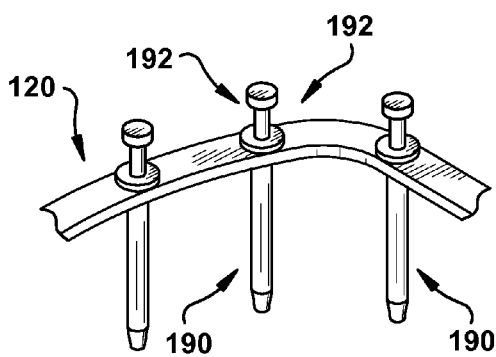
FIG. 7H is a perspective view showing an alternative construction of the penetrating member in FIG. 7C having a plurality of spikes (FIG. 7G) in a non-deployed configuration.
Figure 7I:
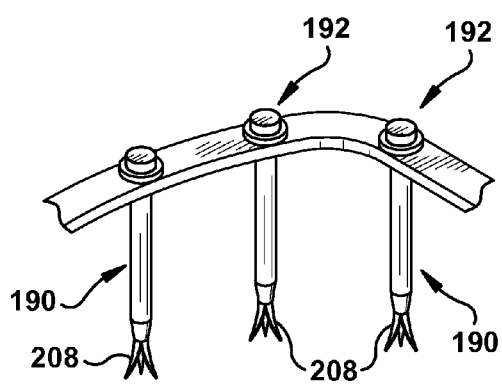
FIG. 7I is a perspective view showing the plurality of spikes in FIG. 7H in a deployed configuration.

An alternative configuration of the penetrating member 120 is shown in FIGS. 7G-I. The penetrating member 120 can include a plurality of spikes 138, each of which comprises a tubular sleeve member 190 and an elongated nail member 192. The sleeve member 190 can include a first end portion 194, a second end portion 196, and a channel 198 extending between the first and second end portions. The first end portion 194 can include an opening for receiving the nail member 192. The second end portion 196 can include sharpened end 200 to facilitate penetration of the sleeve member 190 into cardiac tissue. The sleeve member 190 can be made of a rigid or semi-rigid material, such as a metal or metal alloy.

The nail member 192 can comprise a head portion 202 that is integrally formed with a shaft portion 204. As shown in FIG. 7G, the head portion 202 can have a diameter that is greater than the diameter of the shaft portion 204. The shaft portion 204 can also include a distal end 206 comprising a plurality of resiliently bendable tines 208. The tines 208 are movable from a non-deployed configuration (FIG. 7G) to a deployed configuration (FIG. 7I). The nail member 192 can be made from a rigid or semi-rigid material, such as a metal or metal alloy.

As shown in FIGS. 7G-H, the nail member 192 can be partially inserted into the sleeve member 190 so that the head portion 202 of the nail member is not quite flush with the first end portion 194 of the sleeve member. When the nail member 192 is positioned as shown in FIG. 7H, the tines 208 are friction-fit together within the channel 198 of the sleeve member 190. An axial force can be applied to the head portion 202 of the nail member 192 until movement of the nail member is prevented by contact of the head portion with the first end portion 194 of the sleeve member 190. As shown in FIG. 7I, movement of the distal end 206 out of the channel 198 causes the tines 208 to splay outward and thereby facilitate anchoring of the penetrating member 120 in cardiac tissue.

Figure 8:
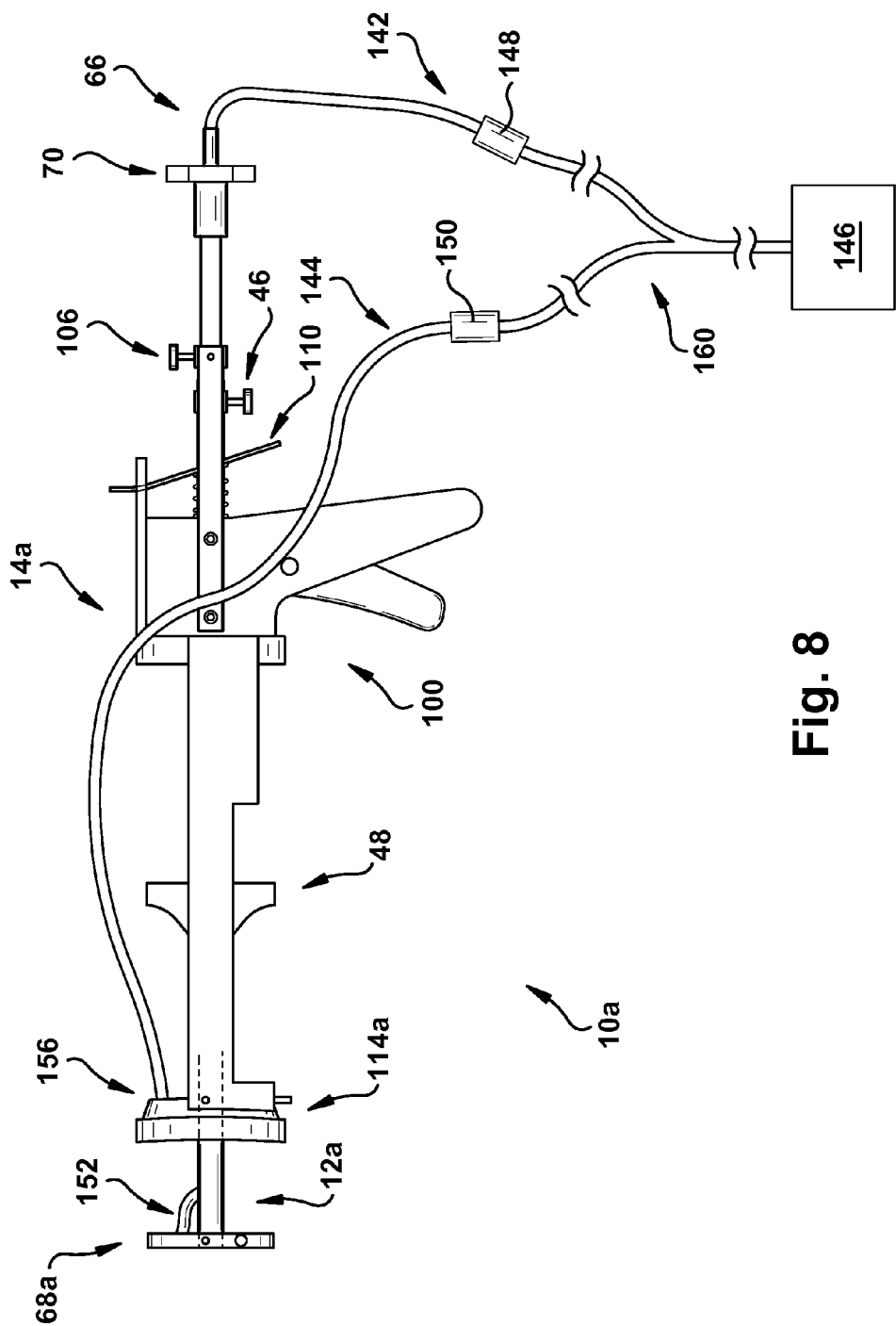
FIG. 8 is a side view showing an apparatus for delivering an implantable medical device to a diseased cardiac valve constructed according to another aspect of the present invention.
Figure 9A:
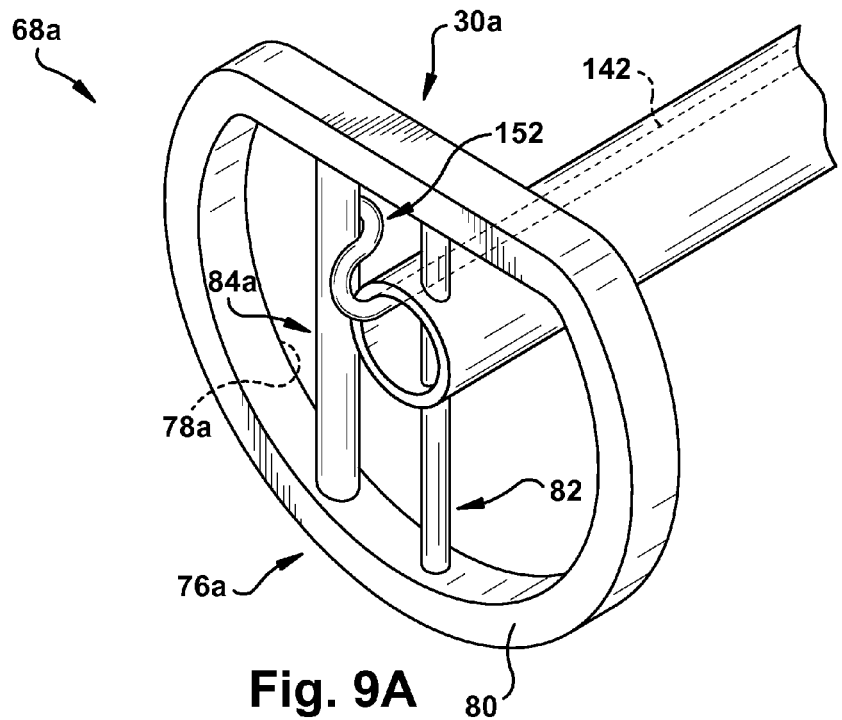
FIG. 9A is an exploded perspective view showing an alternative configuration of the rotatable annular lower support in FIG. 5A.
Figure 9B:
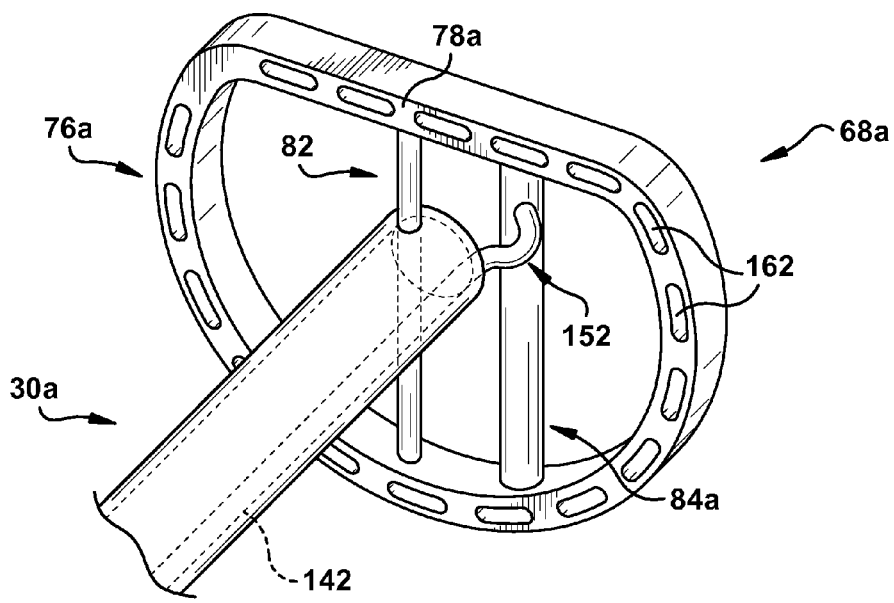
FIG. 9B is an exploded perspective view showing a plurality of vacuum ports dispersed about the rotatable annular lower support in FIG. 9A.
Figure 10:
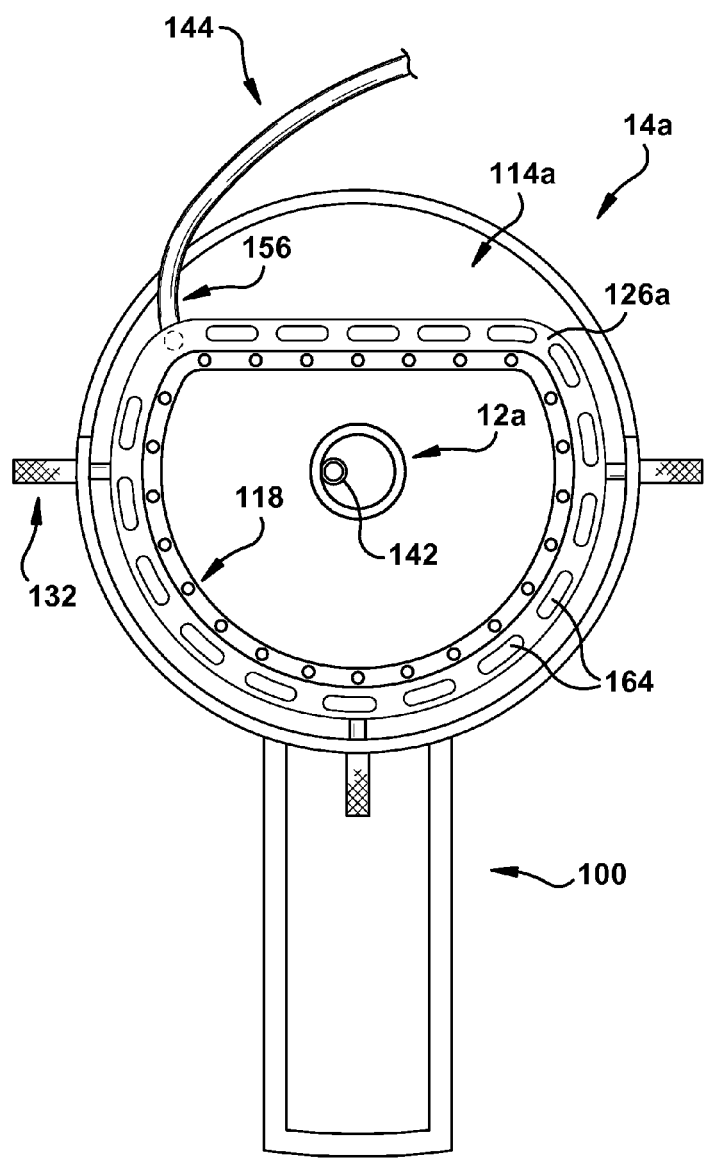
FIG. 10 is a front view showing an alternative configuration of the annular upper support in FIG. 7C affixed (rotatable annular lower support not shown for clarity)

In another aspect of the present invention, an apparatus 10, (FIGS. 8-10) for delivering an implantable medical device 18 (FIG. 12) to a diseased cardiac valve 20 is provided. The apparatus 10, (FIGS. 8-10) is identically constructed as the apparatus 10 shown in FIGS. 1-7, except where as described below. In FIGS. 8-10, structures that are identical to structures in FIGS. 1-7 use the same reference numbers, whereas structures that are similar but not identical carry the suffix "a".

As shown in FIG. 8, the apparatus $10_a$ comprises an elongated shank $12_a$, a brace member $14_a$, a locking mechanism 16, and a vacuum mechanism 140. The vacuum mechanism 140 comprises first and second vacuum lines 142 and 144 operably connected to a vacuum source 146 (e.g., a pump). Each of the first and second vacuum lines 142 and 144 includes first and second clip members 148 and 150, respectively, for controlling pressure in the vacuum lines. The first and second clip members 148 and 150 can be made of plastic, for example, and can be located at any point along the first and second vacuum lines 142 and 144 (respectively). The first and second vacuum lines 142 and 144 can be made of a flexible material, such as Pyrex tubing.

The first vacuum line 142 includes a first end 152 and a second end 154. As shown in FIG. 8, the first vacuum line 142 extends through the channel $62_a$ of the second elongated sleeve $36_a$ to the lower support $68_a$. The first end 152 of the first vacuum line 142 is fluidly connected to the strut member $84_a$ of the lower support $68_a$ (FIGS. 9A-B). The second vacuum line 144 also includes a first end 156 and a second end 158. The second vacuum line 144 extends from the vacuum source 146 to the upper support $114_a$. Although not shown in detail, the second vacuum line 144 can be securely attached at one or more points along the brace member $14_a$ using, for example, a twist tie (not shown). The second end 154 of the first vacuum line 142 and the second end 158 of the second vacuum line 144 each converge at a common junction 160, which is mated to the vacuum source 146.

As shown in FIGS. 9A-B, the lower support $68_a$ includes a plurality of vacuum ports 162 spaced around the upper surface $78_a$ of the annular ring $76_a$. Each of the vacuum ports 162 is fluidly connected via a channel (not shown) in fluid communication with the first vacuum line 142. Although not shown in FIGS. 9A-B, the channel also extends through the strut member $84_a$ so that a vacuum can be applied through the first vacuum line 142, the strut member, and each of the vacuum ports 162. As described in greater detail below, the vacuum ports 162 facilitate stabilization of cardiac tissue surrounding the inferior aspect 24 (FIG. 12) of the diseased cardiac valve 20.

The upper support 114, (FIG. 10) also includes a plurality of vacuum ports 164 spaced around the lower surface $126_a$ of the main annular member $116_a$. Each of the vacuum ports 164 is fluidly connected via a channel (not shown) in fluid communication with the second vacuum line 144. Although not shown in detail, the first end 156 of the second vacuum line 144 is mated with the upper surface $128_a$ of the main annular member $116_a$. It will be appreciated, however, that the first end 156 of the second vacuum line 144 can be mated with other portions of the main annular member $116_a$. As described in greater detail below, the vacuum ports 164 of the main annular member 116, facilitate stabilization of cardiac tissue surrounding the superior aspect 26 (FIG. 12) of the diseased cardiac valve 20.

Figure 11:
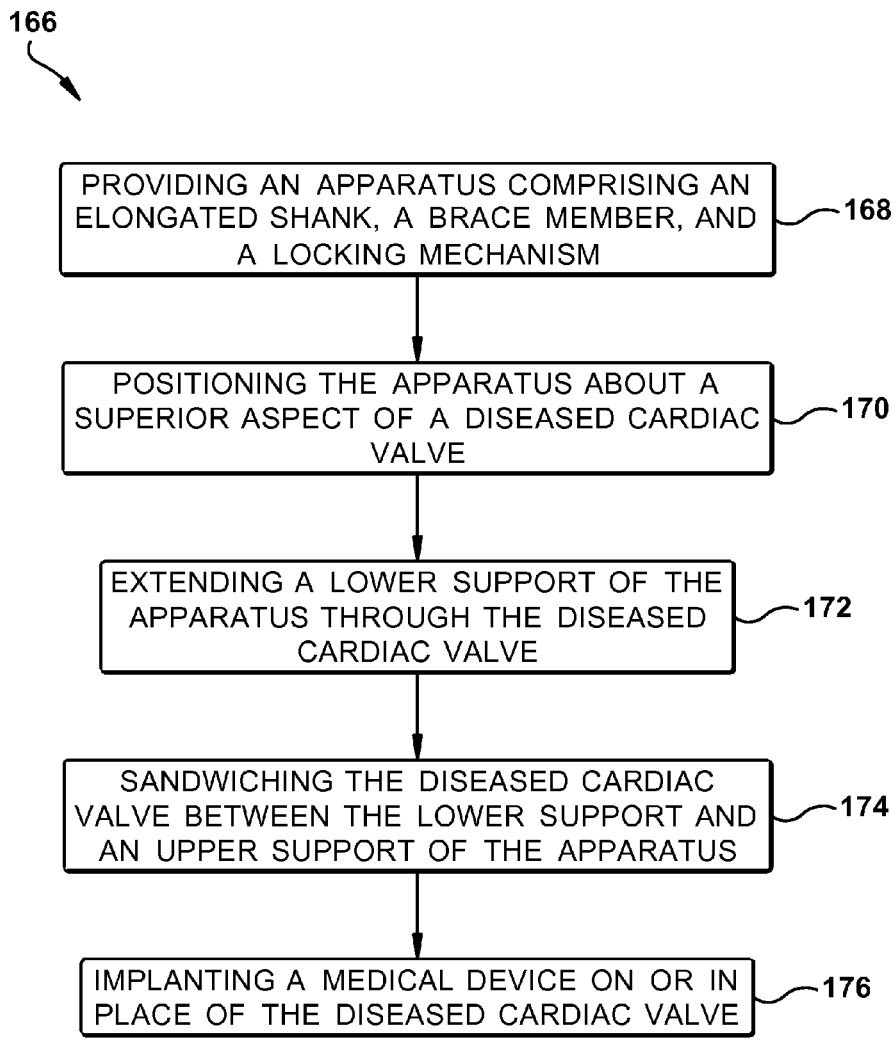
FIG. 11 is a process flow diagram illustrating a method for delivering an implantable medical device to a diseased cardiac valve according to another aspect of the present invention.
Figure 19:
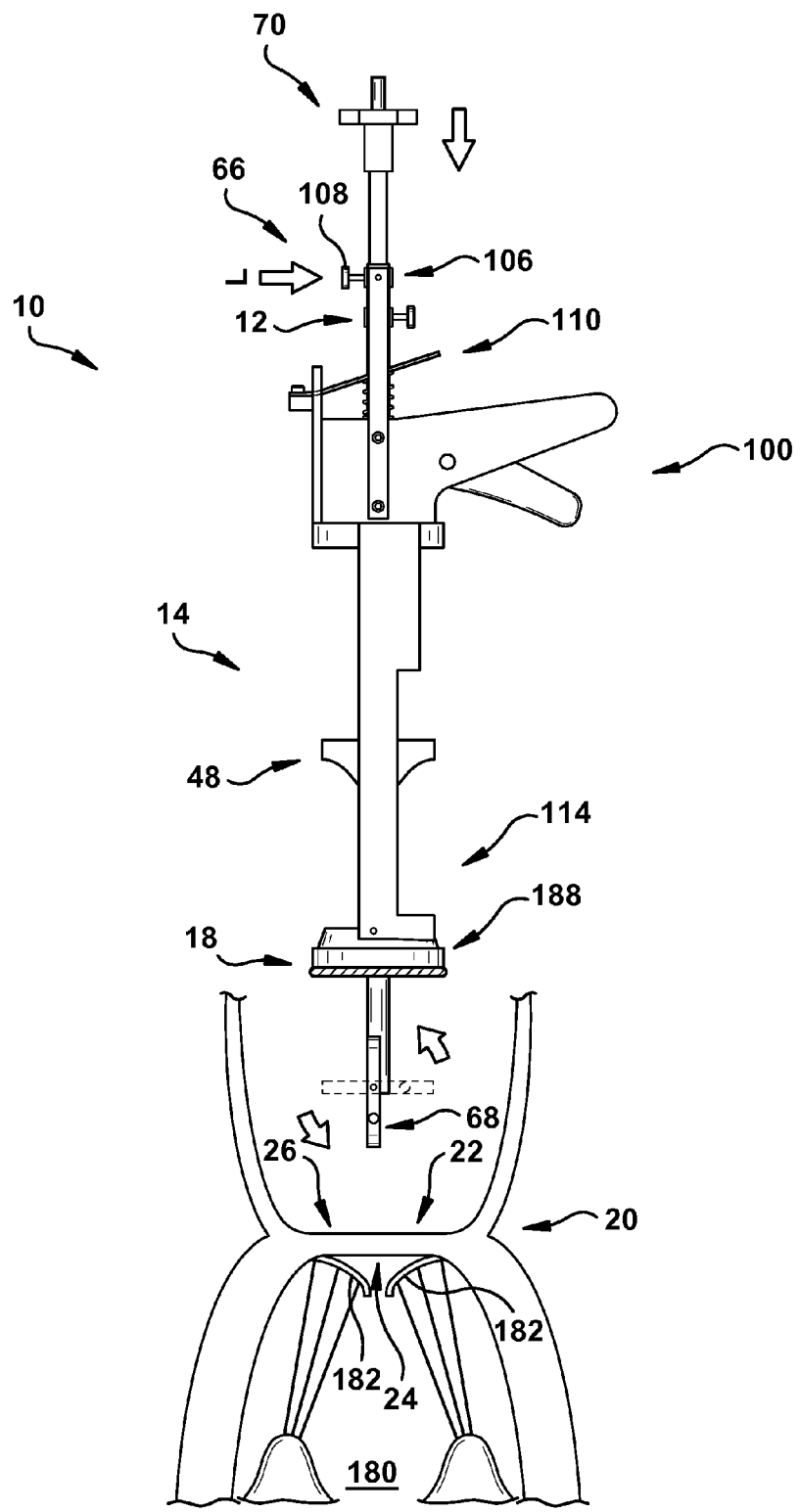
FIG. 19 is a side view similar to FIG. 12 showing the apparatus in FIGS. 1A-B loaded with a prosthetic valve and positioned about a diseased mitral valve.

FIG. 11 is a process flow diagram illustrating another aspect of the present invention comprising a method 166 for delivering an implantable medical device 18 (FIG. 12) to a diseased cardiac valve 20. Although the method 166 is illustrated below for delivering an annuloplasty ring 178 to a diseased mitral valve 22, it will be appreciated that the method can find use in a variety of other applications. For example, it will be appreciated that the method 166 can be used to replace a diseased cardiac valve 20 (e.g., a tricuspid or mitral valve) with a prosthetic valve 188 (FIG. 19).

As shown in FIG. 11, the method 166 includes providing an apparatus 10 comprising an elongated shank 12, a brace member 14, and a locking mechanism 16 at Step 168. One example of the apparatus 10 provided at Step 168 includes the apparatus illustrated in FIGS. 1-7. Prior to use of the apparatus 10, the dimensions of the diseased mitral valve 22 (FIG. 12) will need to be determined. Various methods and devices for determining the dimensions of cardiac valves are known in the art and can include, for example, echocardiogram, computed tomography (CT), magnetic resonance imaging (MRI), fluoroscopy, and angiography.

After determining the dimensions of the diseased mitral valve 22, an appropriately-sized annuloplasty ring 178 is chosen. For example, the chosen annuloplasty ring 178 is sized so that the dimensions of the annuloplasty ring correspond to the dimensions of the mitral annulus (not shown in detail). Next, the annuloplasty ring 178 is secured to the washer member 118 of the upper support 114 using sutures, for example. It will be appreciated, however, that other means can be used to secure the annuloplasty ring 178 to the washer member 118 (e.g., clips, pins, magnets, etc.).

At Step 170, the apparatus 10 is positioned about the superior aspect 26 of the diseased mitral valve 22 during a stopped-heart open chest procedure. As shown in FIG. 12, the apparatus 10 is positioned so that the lower support 68 moves or rotates from the deployed configuration to the non-deployed configuration. To move the lower support 68 between the deployed and non-deployed configurations, the second adjustment screw 108 is first rotated clockwise until the second elongated sleeve 36 is locked in place (indicated by "L"). After the second elongated sleeve 36 is locked in place, an axial force (e.g., using tactile means) is applied to the adjustment member 70 (indicated by arrow) of the lower support adjustment mechanism 66. Application of the axial force causes the lower support 68 to rotate (indicated by arrows) so that the radial plane P of the lower support extends substantially perpendicular to the superior aspect 26 of the diseased mitral valve 22.

Figure 13:
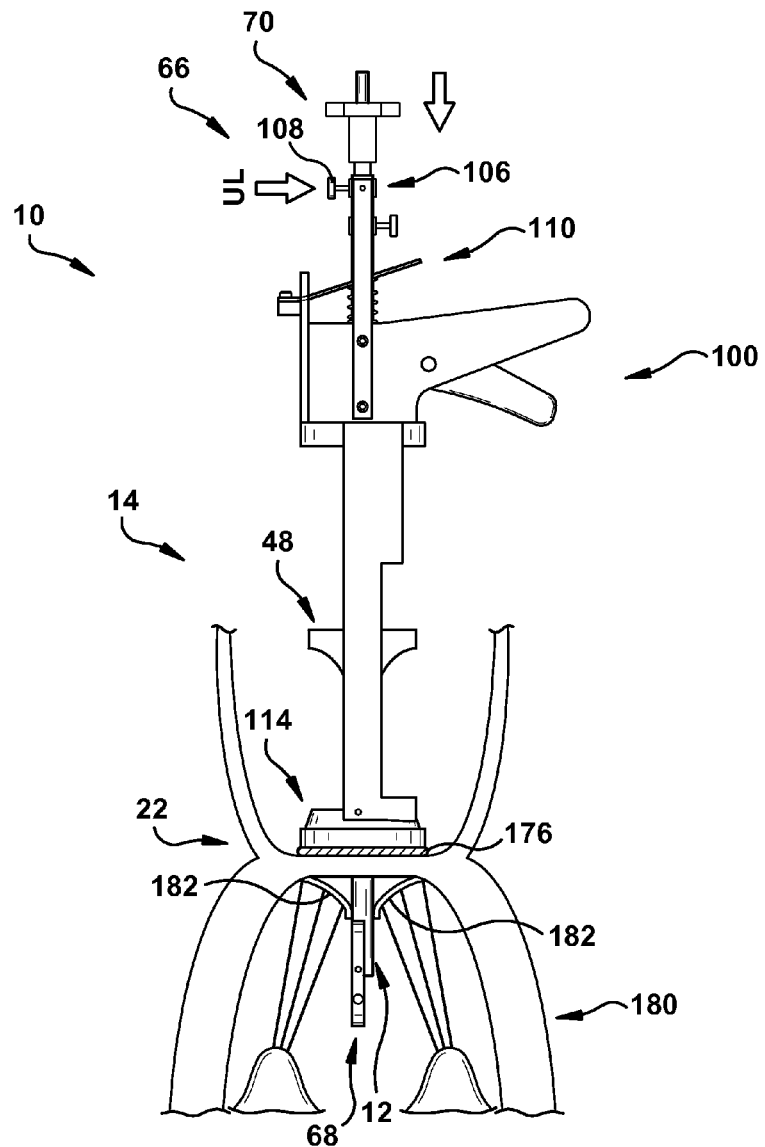
FIG. 13 is a side view showing the elongated shank of the apparatus in FIG. 12 being deployed through the diseased mitral valve.

After rotating the lower support 68 into the non-deployed configuration, the lower support is extended through the diseased mitral valve 22 at Step 172. As shown in FIG. 13, the lower support 68 is moved through the diseased mitral valve 22 by first rotating the second adjustment screw 108 in a counter-clockwise manner to release or unlock (indicated by "UL") the second elongated sleeve 36. An axial force (indicated by arrow) is then applied to the adjustment member 70 so that the second elongated sleeve 36 slides through the channel 42 of the first elongated sleeve 34 and thereby causes the lower support 68 to extend through the diseased mitral valve 22. Before, during, or after extension of the lower support 68 through the diseased mitral valve 22, the apparatus 10 is positioned such that the annuloplasty ring 178 is snugly contacted with the superior aspect 26 of the diseased mitral valve.

Figure 14:
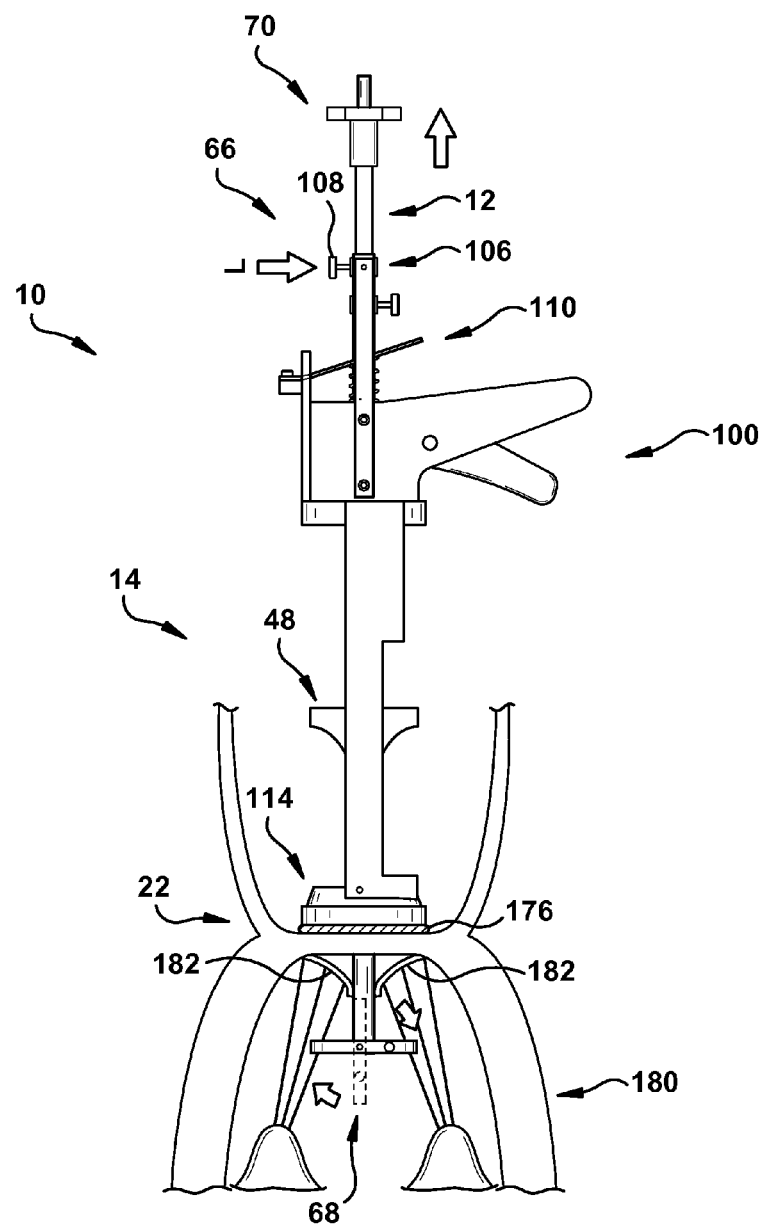
FIG. 14 is a side view showing the lower support in FIG. 13 in a deployed configuration.

Once the lower support 68 is positioned below the diseased mitral valve 22 in the left ventricle 180, the lower support is moved into the deployed configuration. As shown in FIG. 14, lower support 68 is moved into the deployed configuration by first rotating the second adjustment screw 108 in a clockwise manner to lock the second elongated sleeve 36 in place. An axial force is then applied to the adjustment member 70 (indicated by arrow) of the lower support adjustment mechanism 66. Application of the axial force causes the lower support 68 to rotate (indicated by arrows) so that the radial plane P of the lower support extends substantially parallel to the inferior aspect 24 of the diseased mitral valve 22.

Figure 15:
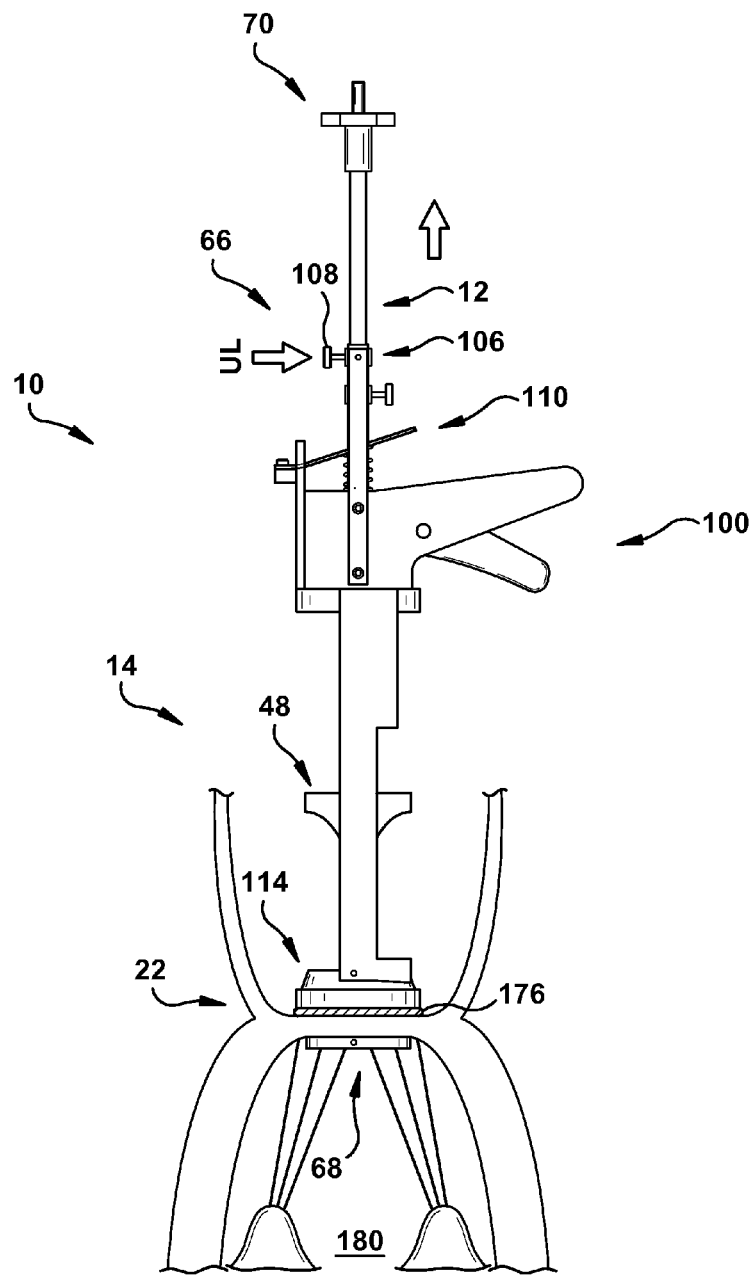
FIG. 15 is a side view showing the diseased cardiac valve in FIG. 14 being sandwiched between the lower support and the annuloplasty ring.

At Step 174, the second adjustment screw 108 is again rotated in a counter-clockwise manner to unlock or release the second elongated sleeve 36 (FIG. 15). Next, an axial force (indicated by arrow) is applied to the second adaptive end portion 74 of the lower support adjustment mechanism 66 so that the second elongated sleeve 36 slides proximally along the first longitudinal axis 32 through the channel 42 of the first elongated sleeve 34. As shown in FIG. 15, application of the axial force causes the lower support 68 to firmly contact the inferior aspect 24 of the diseased mitral valve 22 and thereby sandwich the mitral annulus between the annuloplasty ring 178 and the lower support. Engagement of the lower support 68 with the inferior aspect 24 of the mitral annulus stabilizes the cardiac tissue surrounding the diseased mitral valve 22 and facilitates delivery of the annuloplasty ring 178.

Figure 16:
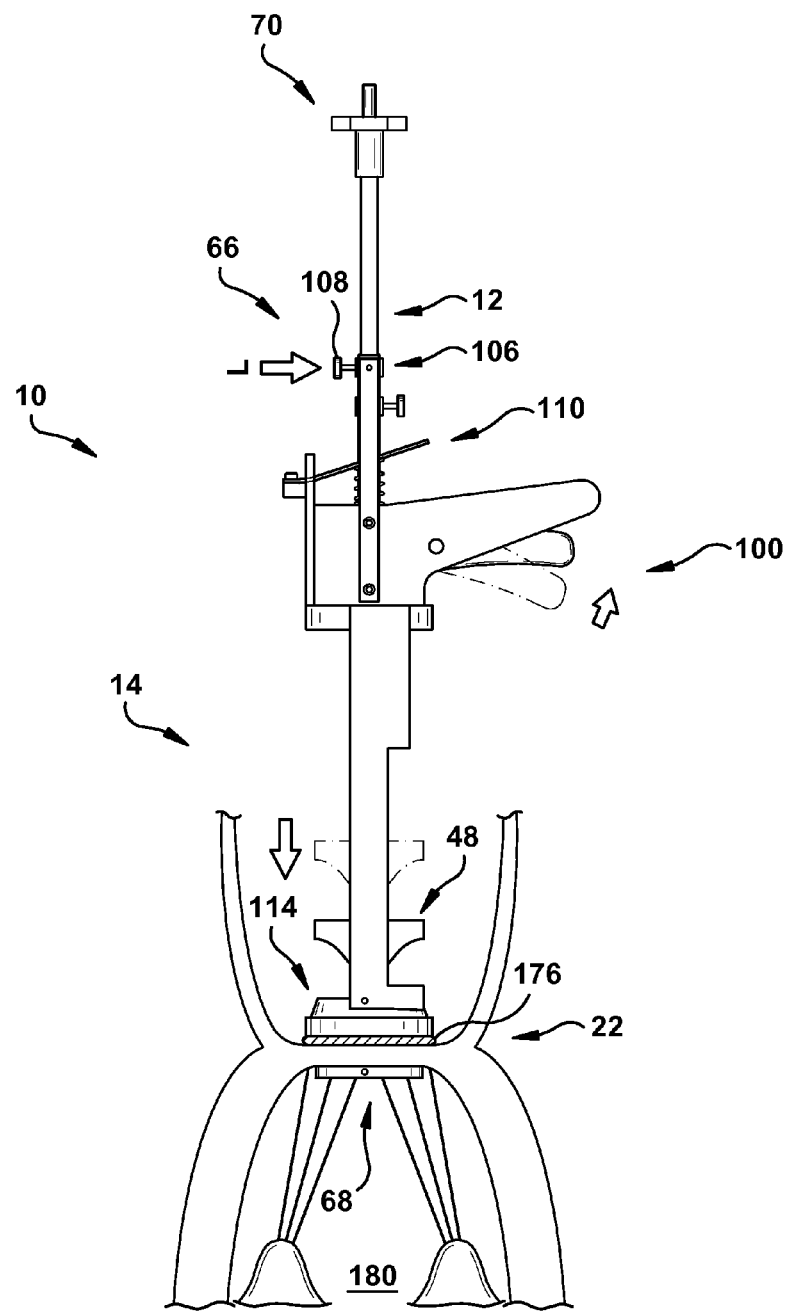
FIG. 16 is a side viewing showing the fixing member of the apparatus in FIG. 15 being deployed to secure the annuloplasty ring to the diseased mitral valve.

To implant the annuloplasty ring 178 on the mitral annulus (Step 176), the actuating handle 100 is operated (i.e., depressed) following placement of the second adjustment screw 108 in the locked position. As shown in FIG. 16, operation of the actuating handle 100 forces the first elongated sleeve 34 to slide in a distal direction over the second elongated sleeve 36. This, in turn, causes the fixing member 48 to progressively move towards the first end portion 86 of the brace member 14 (indicted by arrow). The actuating handle 100 is continuously operated until the mating surface 52 of the fixing member 48 contacts the annular base 136 of the penetrating member 120 and the spikes 138 of the penetrating member are driven through the pores 134 of the washer member 118, through the annuloplasty ring 178, and into the annular tissue. The annuloplasty ring 178 can then be released from the upper support 114 by severing the sutures.

Once the annuloplasty ring 178 has been released from the upper support 114, the annuloplasty ring can be securely sutured in place about the mitral annulus. Implantation of the annuloplasty ring 178 remodels the mitral annulus so that the mitral leaflets 182 properly coapt and thereby mitigate or prevent regurgitation of blood through the mitral valve 22. Proper transvalvular blood flow can be assessed following implantation using one or more techniques known in the art, such as Doppler echocardiography.

Figure 17:
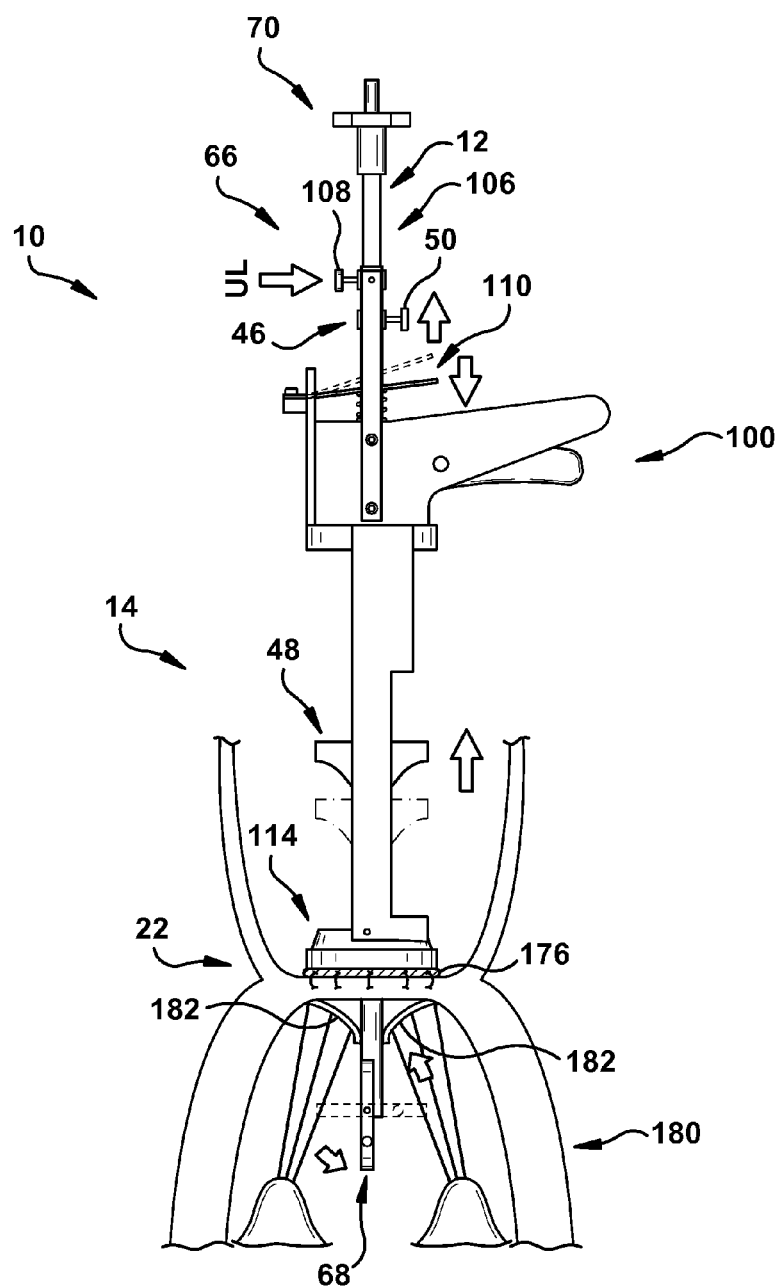
FIG. 17 is a side view showing the apparatus in FIG. 16 being withdrawn following implantation of the annuloplasty ring.

As shown in FIG. 17, the apparatus 10 is removed following successful implantation of the annuloplasty ring 178. To remove the apparatus 10, the lower support 68 is first disengaged from the inferior aspect 24 of the mitral annulus by unlocking the second adjustment screw 108 and applying an axial force to the adjustment member 70 so that the lower support is distanced from the mitral valve 22 in the left ventricle 180. Next, the second adjustment screw 108 is rotated in a clockwise manner to lock the second elongated sleeve 34 in place. An axial force is then applied to the adjustment member 70 so that the lower support 68 obtains the non-deployed configuration (indicated by arrows).

The fixing member 48 is next disengaged from the penetrating member 120 by depressing the lever member 110 (indicated by arrow). With the second adjustment screw 108 in an unlocked configuration, an axial force is then applied to the first locking member 46 so that the first elongated sleeve 34 slides over the second elongated sleeve 36 and causes the fixing member 48 and the lower support 68 to move proximally towards the second end portion 88 of the brace member 14 (indicated by arrows). With the lower support 68 in the non-deployed configuration, the entire apparatus 10 is then completely removed and the operation concluded.

Figure 18:
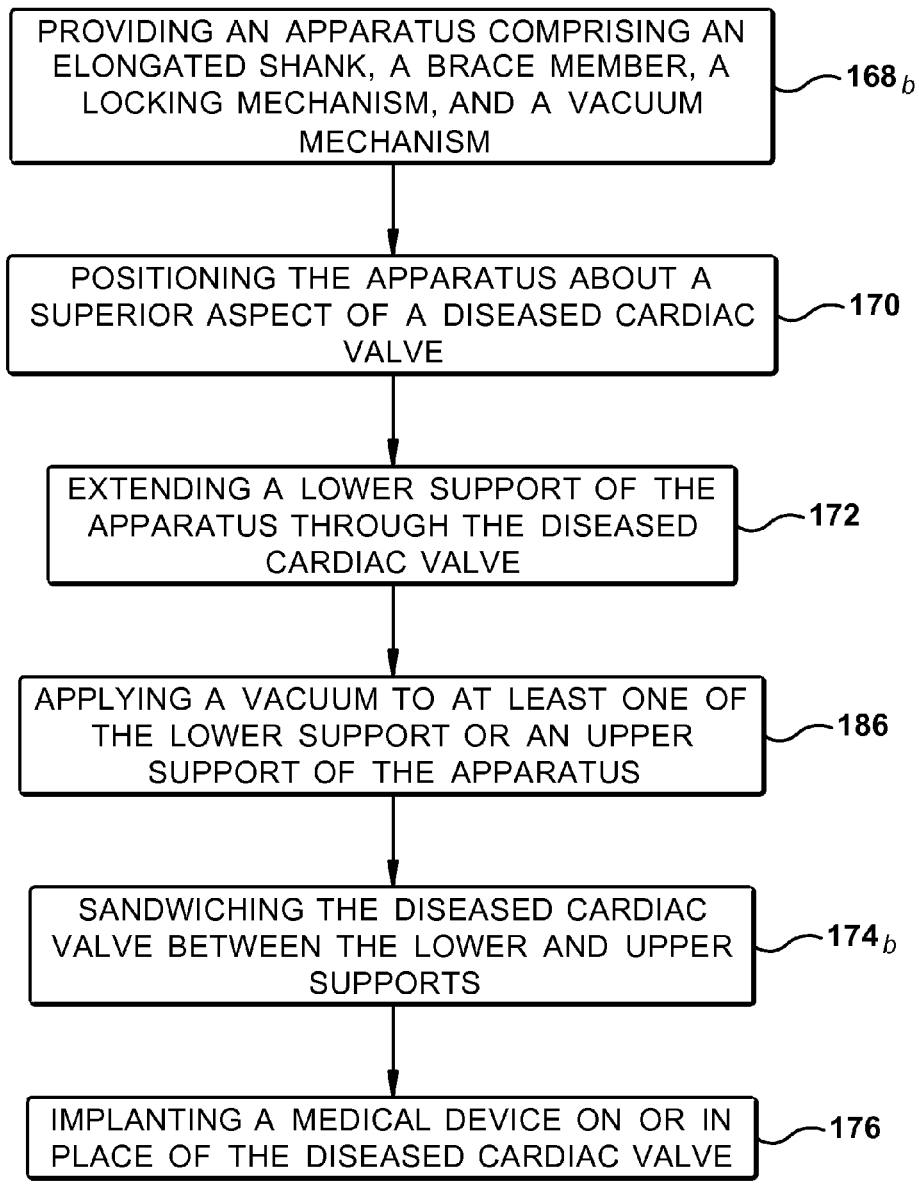
FIG. 18 is a process flow diagram illustrating a method for delivering an implantable medical device to a diseased cardiac valve according to yet another aspect of the present invention.

In another aspect of the present invention, a method 184 (FIG. 18) is provided for delivering an implantable medical device 18 to a diseased cardiac valve 20. The steps of the method 184 are identical to the steps of the method 166 shown in FIG. 11, except where as described below. In FIG. 18, steps that are identical to steps in FIG. 11 use the same reference numbers, whereas steps that are similar but not identical carry the suffix "b". Although the method 184 is illustrated below for delivering an annuloplasty ring 178 to a diseased mitral valve 22, it will be appreciated that the method can find use in a variety of other applications. For example, it will be appreciated that the method 184 can be used to replace a diseased cardiac valve 20 (e.g., a tricuspid or mitral valve) with a prosthetic valve.

As shown in FIG. 18, the method 184 includes providing an apparatus 10, comprising an elongated shank $12_a$, a brace member $14_a$, a locking mechanism 16, and a vacuum mechanism 140 at Step $168_b$. One example of the apparatus $10_a$ provided at Step $168_b$ includes the apparatus illustrated in FIGS. 8-10. Prior to use of the apparatus $10_a$, the dimensions of the diseased mitral valve 22 will need to be determined. As discussed above, various methods and devices for determining the dimensions of cardiac valves are known in the art.

After determining the dimensions of the diseased mitral valve 22, an appropriately-sized annuloplasty ring 178 is chosen. For example, the annuloplasty ring 178 is sized so that the dimensions of the annuloplasty ring correspond to the dimensions of the mitral annulus. Next, the annuloplasty ring 178 is secured to the washer member 118 using sutures, for example. At Step 170, the apparatus $10_a$ is positioned about the superior aspect 26 of the diseased mitral valve 22 during a stopped-heart open chest procedure. As described above, the lower support adjustment mechanism $66_a$ is operated so that the lower support $68_a$ obtains the non-deployed configuration. After moving the lower support $68_a$ into the non-deployed configuration, the lower support is extended through the diseased mitral valve 22 at Step 172 (as described above). Before, during, or after extension of the lower support $68_a$ through the diseased mitral valve 22, each of the first and second clip members 148 and 150 is placed in a closed configuration. After ensuring that each of the first and second clip members 148 and 150 is closed, the vacuum source 146 is then activated.

Next, the annuloplasty ring 178 is moved into contact with the superior aspect 26 of the diseased mitral valve 22. Either before or after contacting the annuloplasty ring 178 with the superior aspect 26 of the diseased mitral valve 22, the first clip member 148 is placed in an open configuration so that suction is applied through the vacuum ports 164 of the main annular member 116, (Step 186). The suction provided through the vacuum ports 164 gently pulls the annular tissue at the superior aspect 26 of the diseased mitral valve 22 into firm contact with the upper support 114, to stabilize the annular tissue during placement of the annuloplasty ring 178. Additionally, application of suction through the vacuum ports 164 helps to ensure that the annuloplasty ring 178 is securely pressed against the mitral annulus.

Once the lower support $68_a$ is positioned in the left ventricle 180 below the diseased mitral valve 22, the lower support is moved into the deployed configuration (as described above). At Step $174_b$, the lower support $68_a$ is firmly contacted with the inferior aspect 24 of the mitral annulus to sandwich the mitral annulus between the annuloplasty ring 178 and the lower support. Either before or after the lower support $68_a$ is contacted with the inferior aspect 24 of the mitral annulus, the second clip member 150 is placed in an open configuration so that suction is applied through the vacuum ports 162 of the lower support $68_a$ (Step 186). The suction provided through the vacuum ports 162 gently pulls the annular tissue at the inferior aspect 24 of the diseased mitral valve 22 into firm contact with the lower support to stabilize the annular tissue during placement of the annuloplasty ring 178.

At Step 176, the annuloplasty ring 178 is implanted about the superior aspect 26 of the diseased mitral valve 22 (as described above). Following successful implantation of the annuloplasty ring 178, each of the first and second clip members 148 and 150 is placed in a closed configuration and the vacuum source 146 deactivated. Once suction has dissipated from the upper and lower supports 114, and 68$_a$, the apparatus 10$_a$ is completely removed (as described above) and the operation concluded. With the annuloplasty ring 178 securely implanted, the mitral annulus is remodeled so that the mitral leaflets 182 properly coapt and thereby mitigate or prevent regurgitation of blood through the mitral valve 22.

Figure 20:
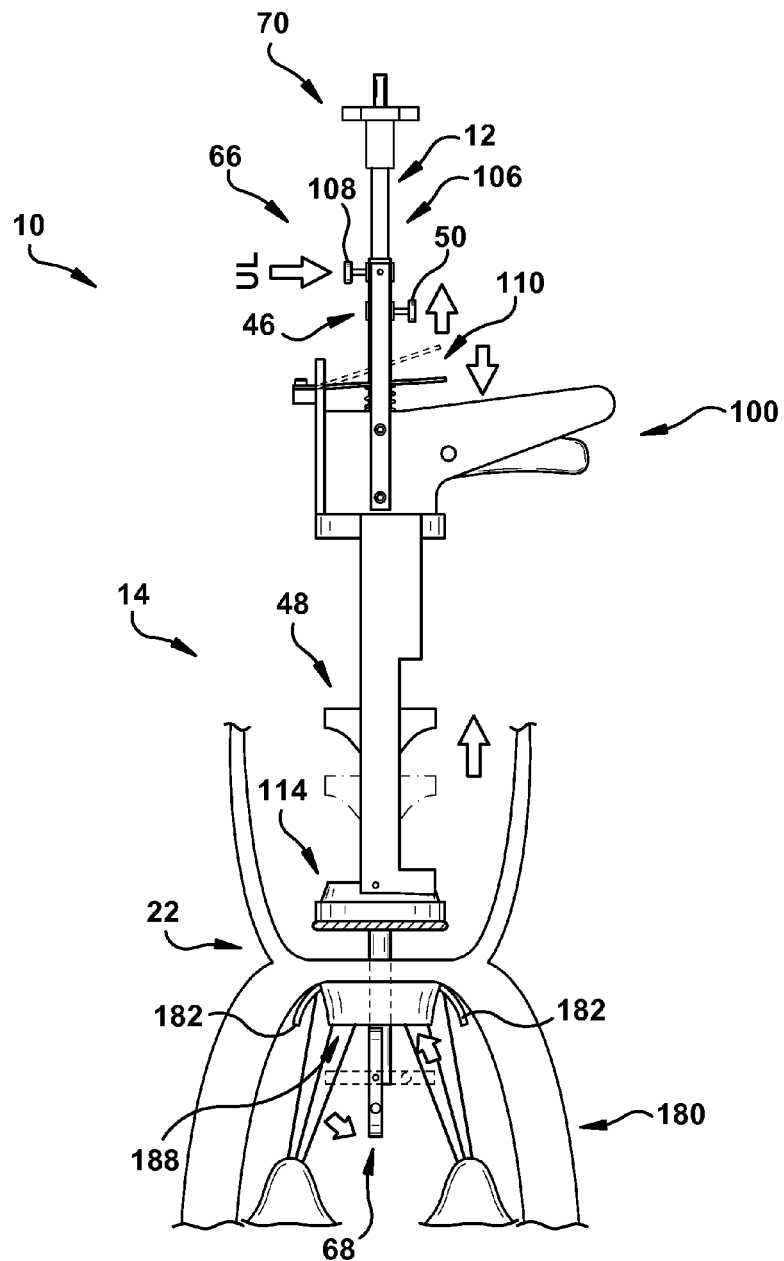
FIG. 20 is a side view showing the apparatus in FIG. 19 being withdrawn following implantation of the prosthetic valve.

It will be appreciated that an implantable medical device 18 other than an annuloplasty ring 178 can be delivered to a diseased cardiac valve 20 using the apparatus 10 and 10$_a$ described above. As shown in FIGS. 19-20, for example, an implantable medical device 18 comprising a prosthetic valve 188 can be delivered to a diseased cardiac valve 20 (e.g., a diseased mitral valve 22). The prosthetic valve 188 can include any mechanical or bioprosthetic heart valve, examples of which are known in the art and can include, but are not limited to, those disclosed in U.S. Pat. No. 5,156,621 and U.S. Patent Pub. Nos. 2006/0195183 A1 and 2006/0259135 A1, the entireties of all of which are hereby incorporated by reference.

The prosthetic valve 188 can be delivered to the diseased mitral valve 22 using either of the methods 166 and 184 described above. Briefly, the method 166 illustrated in FIGS. 11-17 can be used to deliver the prosthetic valve 188 to the diseased mitral valve 22 by first providing the apparatus 10 (FIGS. 1-7) at Step 168. After determining the dimensions of the diseased mitral valve 22 (as described above), an appropriately-sized prosthetic valve 188 is chosen for implantation. Next, the prosthetic valve 188 is secured to the washer member 118 of the upper support 114 using sutures, for example.

At Step 170, the apparatus 10 is positioned about the superior aspect 26 of the diseased mitral valve 22 during a stopped-heart open chest procedure. As shown in FIG. 19, the apparatus 10 is positioned so that the lower support 68 moves or rotates from the deployed configuration to the non-deployed configuration. To move the lower support 68 between the deployed and non-deployed configurations, the second adjustment screw 108 is first rotated clockwise until the second elongated sleeve 36 is locked in place (indicated by "L"). After the second elongated sleeve 36 is locked in place, an axial force (e.g., using tactile means) is applied to the adjustment member 70 (indicated by arrow) of the lower support adjustment mechanism 66. Application of the axial force causes the lower support 68 to rotate (indicated by arrows) so that the radial plane P of the lower support extends substantially perpendicular to the superior aspect 26 of the diseased mitral valve 22.

After rotating the lower support 68 into the non-deployed configuration, the lower support is extended through the diseased mitral valve 22 at Step 172 (as described above). Once the lower support 68 is positioned below the diseased mitral valve 22 in the left ventricle 180, the lower support is moved into the deployed configuration by first rotating the second adjustment screw 108 in a clockwise manner to lock the second elongated sleeve 36 in place. An axial force is then applied to the adjustment member 70 of the lower support adjustment mechanism 66. Application of the axial force causes the lower support 68 to rotate so that the radial plane P of the lower support extends substantially parallel to the inferior aspect 24 of the diseased mitral valve 22.

At Step 174, the second adjustment screw 108 is again rotated in a counter-clockwise manner to unlock or release the second elongated sleeve 36 and, as described above, thereby cause the lower support 68 to engage the inferior aspect 24 of the mitral annulus to stabilize the cardiac tissue surrounding the diseased mitral valve 22 and facilitate delivery of the prosthetic valve 188. Next, the actuating handle 100 is operated (i.e., depressed) after placing the second adjustment screw 108 in the locked position. As described above, the actuating handle 100 is continuously operated until the mating surface 52 of the fixing member 48 contacts the annular base 136 of the penetrating member 120 and the spikes 138 of the penetrating member are driven through the pores 134 of the washer member 118, through the prosthetic valve 188, and into the annular tissue.

As shown in FIG. 20, placement of the prosthetic valve 188 over the diseased mitral valve 22 causes the mitral leaflets 182 to splay outward against the ventricular walls. Before, during, or after placement of the prosthetic valve 188 over the diseased mitral valve 22, the chordae can be severed. Alternatively, the chordae can be left intact. After properly positioning the prosthetic valve 188 (i.e., to ensure proper blood flow therethrough), the prosthetic valve can be released from the upper support 114 by severing the sutures and, if necessary, further securing the prosthetic valve in place.

As described above, the apparatus 10 is removed following successful implantation of the prosthetic valve 188. As shown in FIG. 20, for example, the lower support 68 is first disengaged from the inferior aspect 24 of the mitral annulus by unlocking the second adjustment screw 108 and applying an axial force to the adjustment member 70 so that the lower support is distanced from the mitral valve 22 in the left ventricle 180. Next, the second adjustment screw 108 is rotated in a clockwise manner to lock the second elongated sleeve 34 in place. An axial force is then applied to the adjustment member 70 so that the lower support 68 obtains the non-deployed configuration (indicated by arrows).

The fixing member 48 is next disengaged from the penetrating member 120 by depressing the lever member 110 (indicated by arrow). With the second adjustment screw 108 in an unlocked configuration, an axial force is then applied to the first locking member 46 so that the first elongated sleeve 34 slides over the second elongated sleeve 36 and causes the fixing member 48 and the lower support 68 to move proximally towards the second end portion 88 of the brace member 14 (indicated by arrows). With the lower support 68 in the non-deployed configuration, the entire apparatus 10 is then completely removed and the operation concluded.

In another aspect of the present invention, an apparatus 10$_b$ (FIGS. 21-25B) is provided for delivering an implantable medical device 18 to a diseased cardiac valve 20. The apparatus 10$_b$ is identically constructed as the apparatus 10 shown in FIGS. 1-7, except where as described below. In FIGS. 21-25B, structures that are identical to structures in FIGS. 1-7 use the same reference numbers, whereas structures that are similar but not identical carry the suffix "b".

Figure 21:
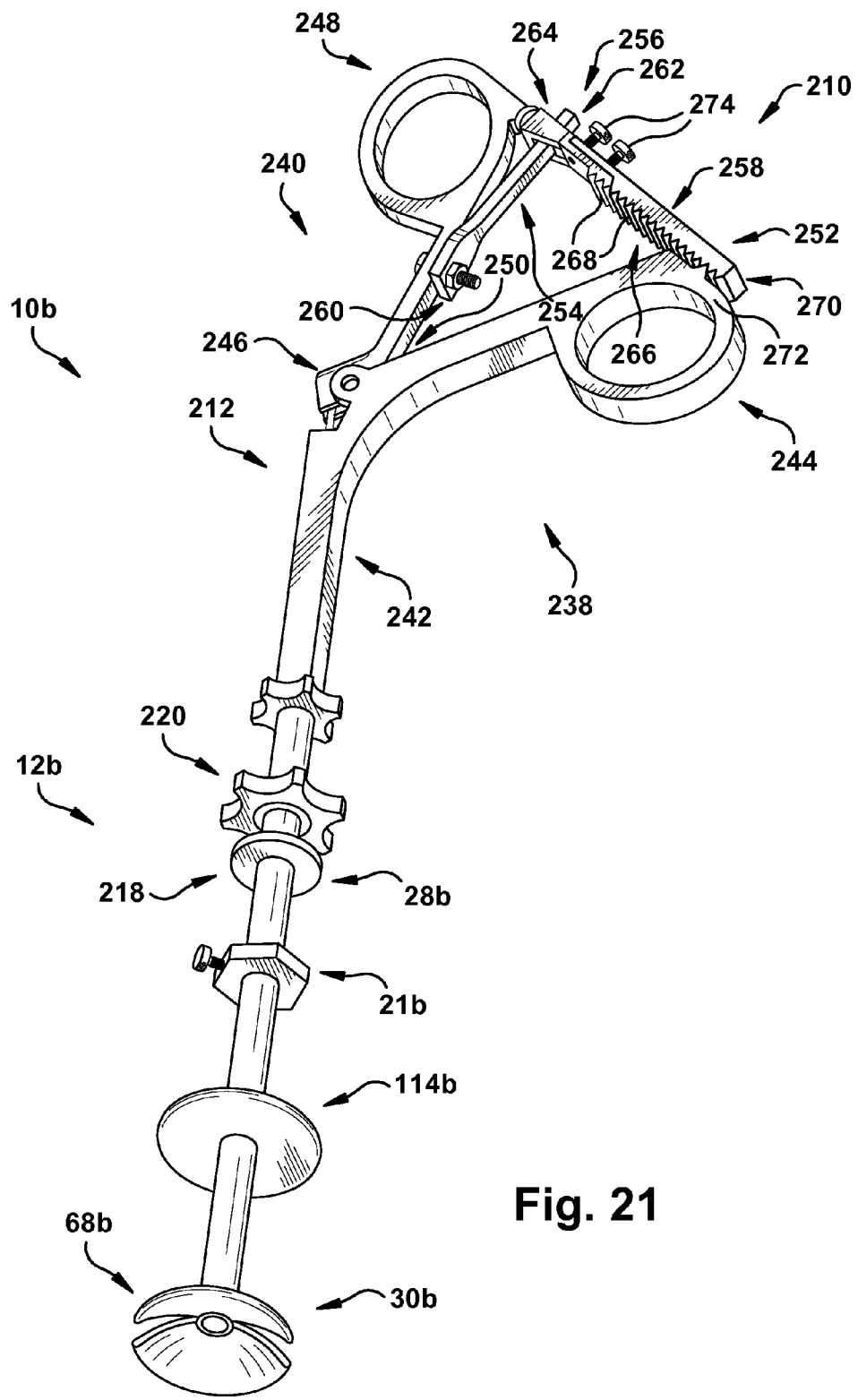
FIG. 21 is a perspective view of an apparatus for delivering an implantable medical device to a diseased cardiac valve constructed according to another aspect of the present invention, the apparatus comprising an elongated shank, an actuating handle, and a drive system.
Figure 22:
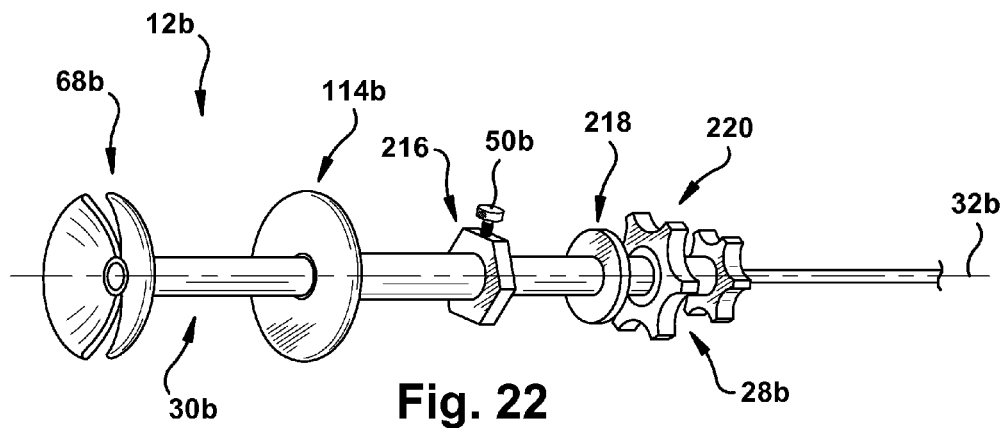
FIG. 22 is a perspective view of the elongated shank in FIG. 21.
Figure 23:
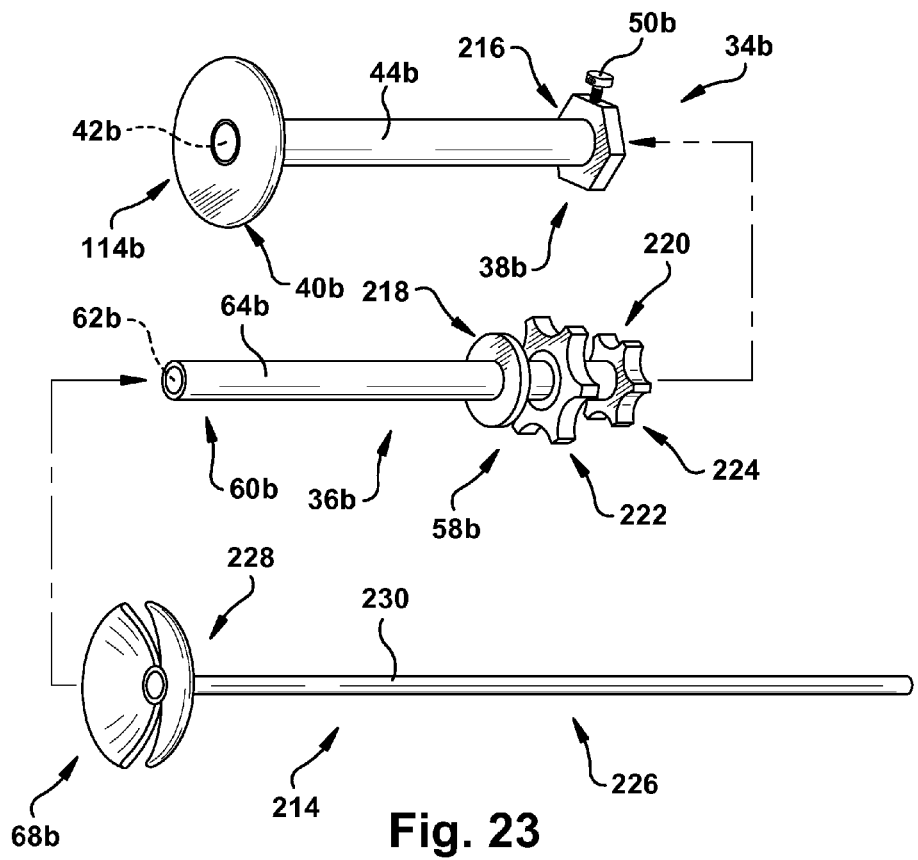
FIG. 23 is a perspective view of the elongated shank shown in FIG. 22 in an exploded configuration.
Figure 24A:
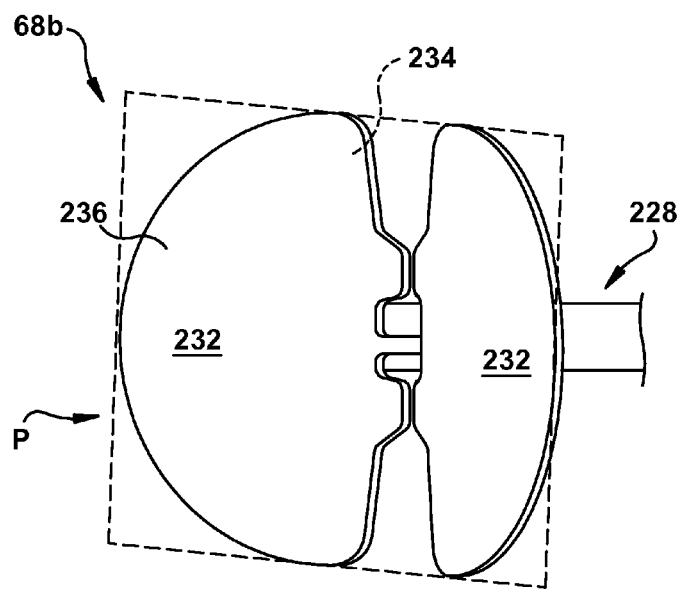
FIG. 24A is a perspective view of a lower support in an expanded configuration constructed according to another aspect of the present invention.
Figure 24B:
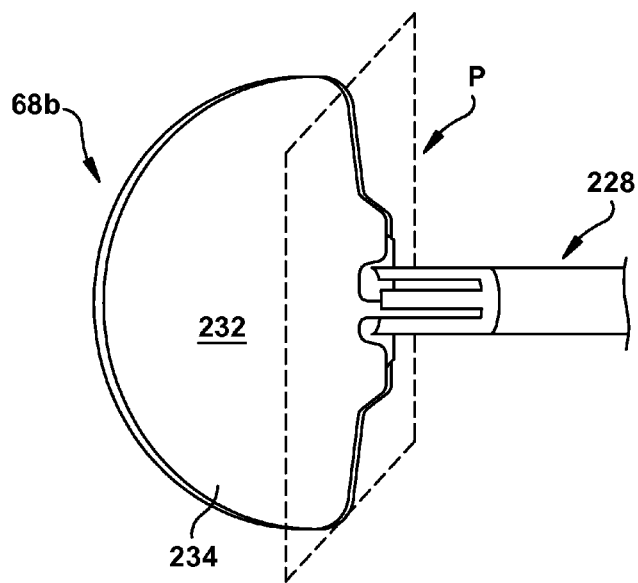
FIG. 24B is a perspective view of the lower support in FIG. 24A in a collapsed configuration.
Figure 24C:
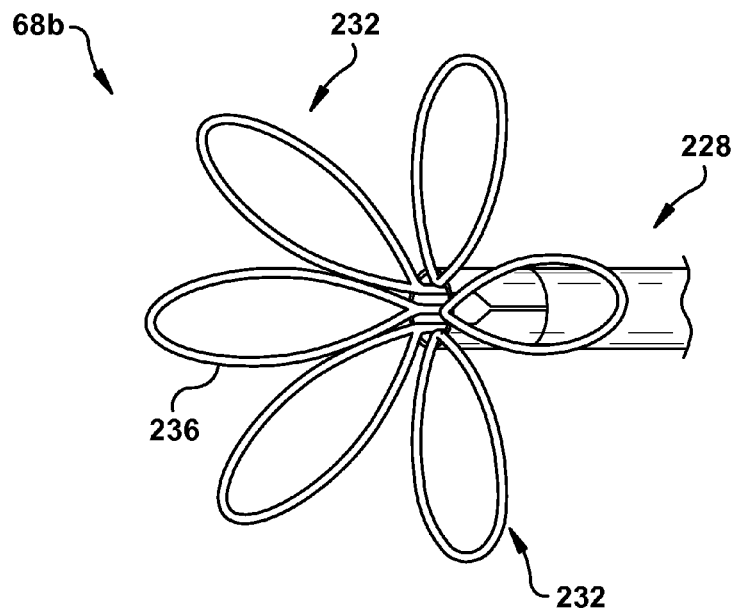
FIG. 24C is a perspective view showing an alternative construction of the lower support in FIG. 24A.
Figure 24D:
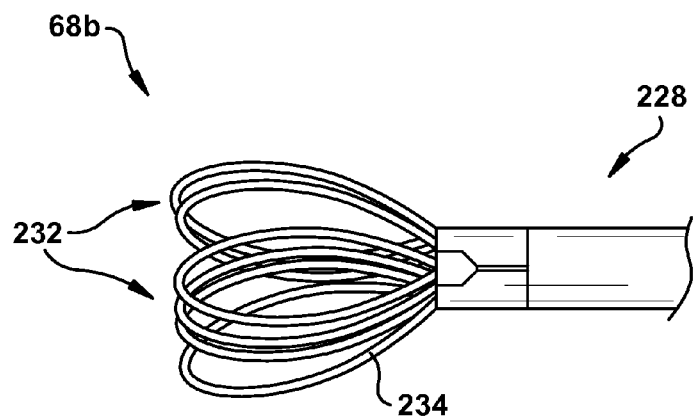
FIG. 24D is a perspective view of the lower support shown in FIG. 24C in a collapsed configuration.

As shown in FIG. 21, the apparatus 10$_b$ comprises an elongated shank 12$_b$, an actuating handle 210, and a drive system 212. The elongated shank 12$_b$ (FIG. 22) comprises a first end portion 28$_b$, a second end portion 30$_b$, and a first longitudinal axis 32$_b$ extending between the first and second end portions. As shown in FIG. 23, the elongated shank 12$_b$ is formed from a first elongated sleeve 34$_b$, a second elongated sleeve 36$_b$, and a third elongated sleeve 214. The first elongated sleeve 34$_b$ includes oppositely disposed first and second ends 38$_b$ and $40_b$, and a first channel $42_b$ extending between the first and second ends. The first channel $42_b$ is defined by an outer surface $44_b$ oppositely disposed from an inner surface (not shown) and is adapted to receive the second elongated sleeve $36_b$. All or only a portion of the first elongated sleeve $34_b$ can be made of a rigid material, such as a metal or metal alloy.

The first and second ends $38_b$ and $40_b$ of the first elongated sleeve $34_b$ respectively include a locking member 216 and an upper support $114_b$. The locking member 216 has a ring-shaped or bolt-like configuration. As shown in FIG. 23, for example, the locking member 216 has a hexagonal configuration; however, it will be appreciated that the locking member can have any desired geometry. The locking member 216 is securely attached to the outer surface $44_b$ of the first elongated sleeve $34_b$ via an adjustment screw $50_b$. The adjustment screw $50_b$ extends through the locking member 216, into contact with the outer surface $44_b$, and into the first channel $42_b$ of the first elongated sleeve $34_b$. It will be appreciated that the locking member 216 can include more than one adjustment screw $50_b$. The locking member 216 can be made of a rigid material, such as a metal or metal alloy.

The upper support $114_b$ can have a similar or identical construction as the upper support 114 and 114, described above. For example, the upper support $114_b$ can have an annular shape and be adapted for receiving the implantable medical device 18. The upper support $114_b$ is securely connected to the second end $40_b$ of the first elongated sleeve $34_b$. Although not shown in FIGS. 21-23, it will be appreciated that the upper support $114_b$ can comprise a main annular member 116, a penetrating member 120, and a washer member 118 (as described above).

The second elongated sleeve $36_b$ includes oppositely disposed first and second ends $58_b$ and $60_b$, and a second channel $62_b$ extending between the first and second ends. The second channel $62_b$ is defined by an outer surface $64_b$ oppositely disposed from an inner surface (not shown). Additionally, the second channel $62_b$ is adapted to receive the third elongated sleeve 214. All or only a portion of the second elongated sleeve $36_b$ can be made of a rigid material, such as a metal or metal alloy.

As shown in FIG. 23, the first end $58_b$ of the second elongated sleeve $36_b$ includes a directional marker 218 and a rotation handle 220. The directional marker 218 has an annular configuration is rotatably connected about the outer surface $64_b$ of the second elongated sleeve $36_b$. As described below in more detail, the directional marker 218 can be rotated about the second elongated sleeve $36_b$ to facilitate proper orientation of the lower support $68_b$ during implantation of the implantable medical device 18. The directional marker 218 can be made of rigid material, such a metal, metal alloy, or hardened plastic.

The rotation handle 220 comprises first and second rotation members 222 and 224 for rotating the lower support $68_b$. Each of the first and second rotation members 222 and 224 has a star-shaped configuration; however, it will be appreciated that the rotation members can have any shape or configuration suitable to facilitate application of tactile force thereto. The first and second rotation members 222 and 224 are securely connected to the outer surface $64_b$ of the second elongated sleeve $36_b$. All or only a portion of the first rotation member 222 and/or the second rotation member 224 can be made of a rigid material, such as a metal, metal alloy, or hardened plastic.

The third elongated sleeve 214 includes oppositely disposed first and second ends 226 and 228. The third elongated sleeve 214 can have a solid construction or, alternatively, include a channel (not shown) that extends between the first and second ends 226 and 228. The third elongated sleeve 214 includes an outer surface 230, which is adapted for mating with the second channel $62_b$ of the second elongated sleeve $36_b$. All or only a portion of the third elongated sleeve 214 can be made of a rigid material, such as a metal or metal alloy.

Figures 25A, 25B:
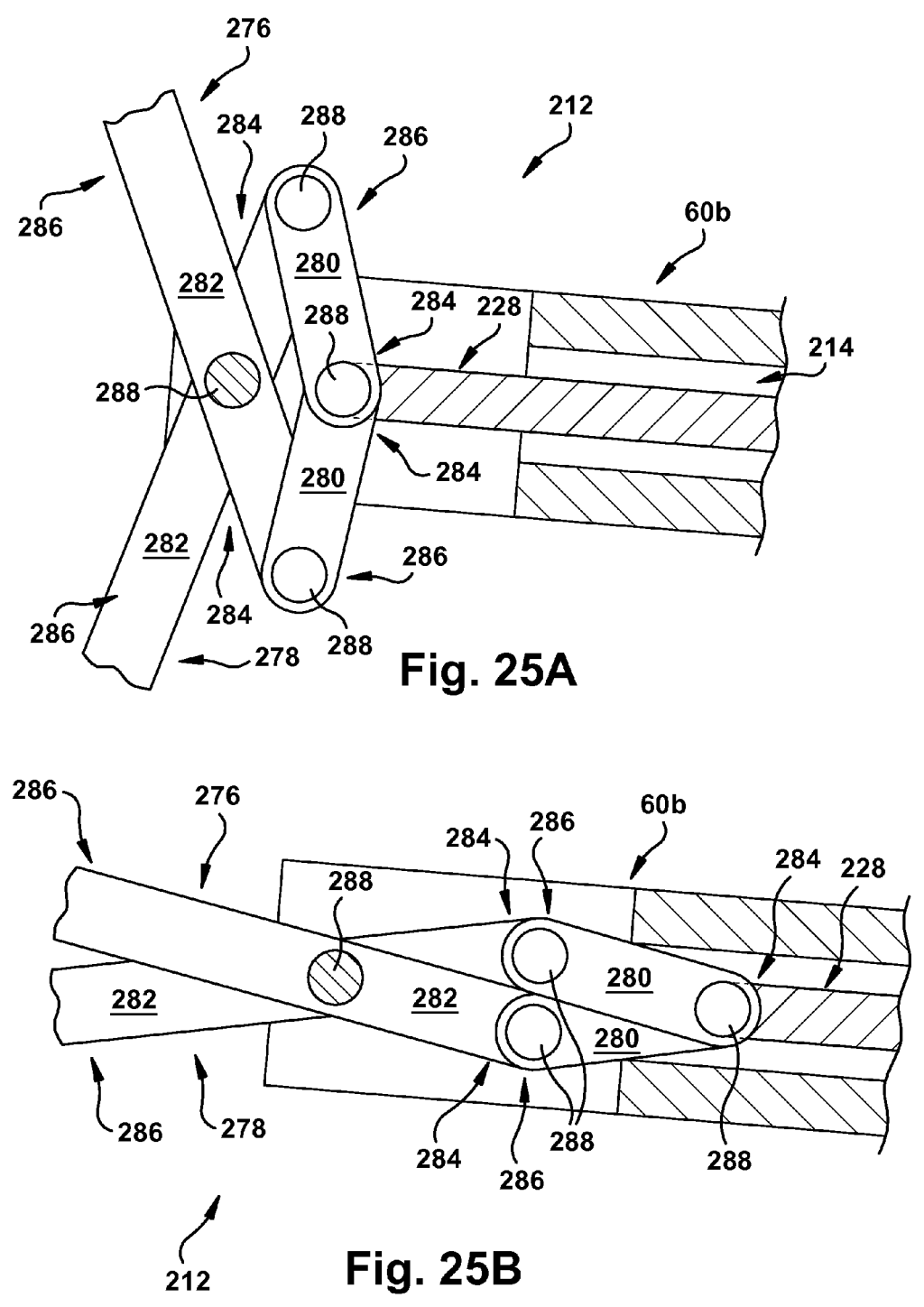

The second end 228 of the third elongated sleeve 214 includes the lower support $68_b$. The lower support $68_b$ (FIGS. 24A-B) has a butterfly-shaped configuration and includes at least two opposable fingers 232 that are movable from an expanded configuration (FIG. 24A) to a collapsed configuration (FIG. 24B) via the drive system 212 (FIGS. 25A-B). Each of the opposable fingers 232 (FIGS. 24A-B) has a semi-circular shape and includes oppositely disposed upper and lower surfaces 234 and 236. The opposable fingers 232 form a plane P that extends radially between the upper and lower surfaces 234 and 236. It will be appreciated that the opposable fingers 232 can have other configurations, such as the one shown in FIGS. 24C-D. As described in more detail below, the upper surface 234 (FIGS. 24A-B) of each of the fingers 232 is adapted for contacting an inferior aspect 24 of the diseased cardiac valve 20. The opposable fingers 232 can be made of any suitable rigid or semi-rigid material, such as a metal, a metal alloy, hardened plastic(s), or flexible polymer(s).

Referring again to FIG. 21, the actuating handle 210 comprises opposable first and second lever arms 238 and 240. The first lever arm 238 includes a curved first end portion 242 and a ring-shaped second end portion 244 for handling the apparatus $10_b$. The second lever arm 240 also includes a curved first end portion 246 and a ring-shaped second end portion 248 for handling the apparatus $10_b$. As shown in FIG. 21, the first end portion 246 of the second lever arm 240 is operably connected to the first end 226 of the third elongated sleeve 214. The first and second lever arms 238 and 240 are flexibly joined via a hinge mechanism 250.

The actuating handle 210 also includes a sliding lock mechanism 252 for securing the lower support $68_b$ in a desired configuration (i.e., an expanded or collapsed configuration) during operation of the apparatus $10_b$. As shown in FIG. 21, the sliding lock mechanism 252 comprises a club-shaped joint member 254, a hinge member 256, and a locking member 258. The joint member 254 includes first and second ends 260 and 262 respectively connected to the second lever arm 240 and the hinge member 256. The hinge member 256 is connected to the second lever arm 240 and is mated with a first end 264 of the locking member 258.

The locking member 258 includes a mating surface 266 having a plurality of ridges 268 that extend between the first end 264 and a second end 270. The mating surface 266 of the locking member 258 is capable of receiving a mating end 272 of the first lever arm 238. As shown in FIG. 21, the locking member 258 also includes at least one screw 274 for adjusting the position of the first and second lever arms 238 and 240.

The drive system 212 (FIGS. 25A-B) generally comprises a scissor jack mechanism for transitioning the lower support $68_b$ between the expanded and collapsed configurations. As shown in FIGS. 25A-B, the drive system 212 comprises first and second opposable arm members 276 and 278 operatively connected to the second end 228 of the third elongated sleeve 214. Each of the first and second arm members comprises first and second segments 280 and 282 having first and second ends 284 and 286. Although not shown in FIGS. 25A-B, the second ends 286 of each of the second segments 282 is operatively connected to a respective one of the opposable fingers 232. The first and second arm members 276 and 278 can be made of a rigid material, such as a metal, a metal alloy, or a hardened plastic.

The first and second arm members 276 and 278 are flexibly joined together at a plurality of joints 288. For example, the second segment 282 of the first arm member 276 is joined to the second segment of the second arm member 278 via a pin (not shown in detail) located intermediate the first and second ends 284 and 286 of the second segment. As shown in FIGS. 25A-B, the first and second arm members 276 and 278 are operatively coupled to the second end 228 of the third elongated sleeve 214 via a pin (not shown in detail). In operation, application of a longitudinal force at the first end 226 of the third elongated sleeve 214 (i.e., towards the second end 228 of the third elongated sleeve) spreads the first and second arm members 276 and 278 and thereby causes the lower support $68_b$ to obtain the expanded configuration. Conversely, application of a longitudinal force at the first end 226 of the third elongated sleeve 214 (i.e., towards the actuating handle 210) brings the first and second arm members 276 and 278 together and thereby causes the lower support $68_b$ to obtain the collapsed configuration.

Figure 26:
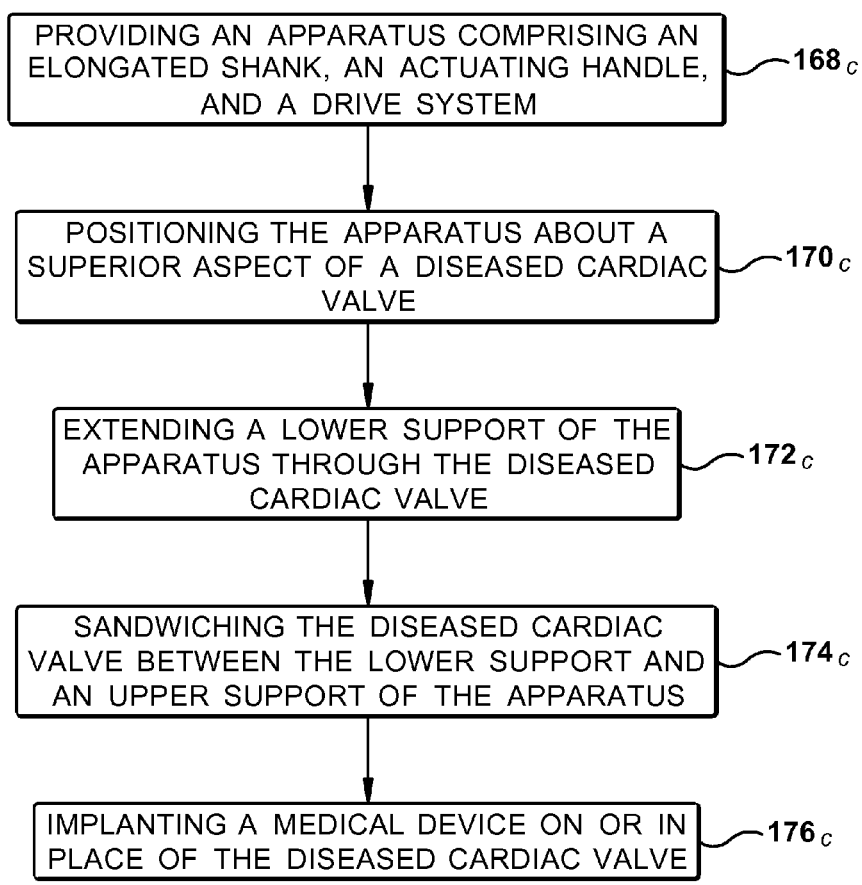
FIG. 26 is a process flow diagram illustrating a method for delivering an implantable medical device to a diseased cardiac valve according to yet another aspect of the present invention.

In another aspect of the present invention, a method 290 (FIG. 26) is provided for delivering an implantable medical device 18 to a diseased cardiac valve 20. The steps of the method 290 are identical to the steps of the method 166 shown in FIG. 11, except where as described below. In FIG. 26, steps that are identical to steps in FIG. 11 use the same reference numbers, whereas steps that are similar but not identical carry the suffix "c". Although the method 290 is illustrated below for delivering an annuloplasty ring 178 to a diseased mitral valve 22, it will be appreciated that the method can find use in a variety of other applications. For example, it will be appreciated that the method 290 can be used to replace a diseased cardiac valve 20 (e.g., a tricuspid or mitral valve) with a prosthetic valve 188.

As shown in FIG. 26, the method 290 includes providing an apparatus $10_b$ comprising an elongated shank $12_b$, an actuating handle 210, and a drive system 212 at Step $168_c$. One example of the apparatus $10_b$ provided at Step 168, includes the apparatus illustrated in FIGS. 21-25B. Prior to use of the apparatus $10_b$, the dimensions of the diseased mitral valve 22 (FIG. 27) will need to be determined. Various methods and devices for determining the dimensions of cardiac valves are known in the art and can include, for example, echocardiogram, CT, MRI, fluoroscopy and angiography.

After determining the dimensions of the diseased mitral valve 22, an appropriately-sized annuloplasty ring 178 is chosen. For example, the chosen annuloplasty ring 178 is sized so that the dimensions of the annuloplasty ring correspond to the dimensions of the mitral annulus (not shown in detail). Next, the annuloplasty ring 178 is secured to the upper support $114_b$ using sutures, for example. It will be appreciated that other means can be used to secure the annuloplasty ring 178 to the upper support $114_b$ (e.g., clips, pins, magnets, etc.).

Figure 27:
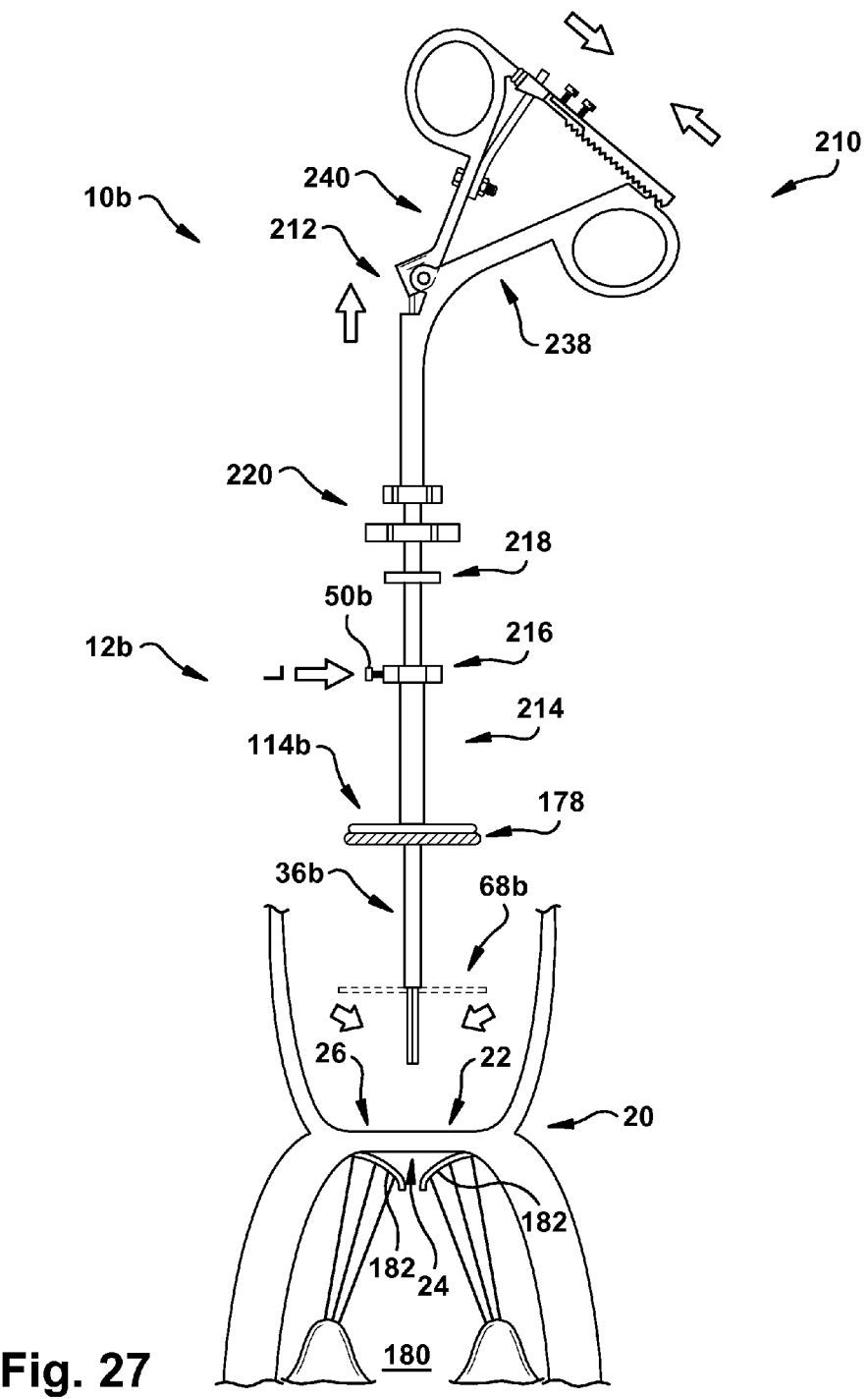
FIG. 27 is a side view of the apparatus in FIG. 21 loaded with an annuloplasty ring and positioned about a diseased mitral valve.

At Step $170_c$, the apparatus $10_b$ is positioned about the superior aspect 26 of the diseased mitral valve 22 during a stopped-heart open chest procedure. As shown in FIG. 27, the apparatus $10_b$ is positioned so that the lower support $68_b$ moves or rotates from the expanded configuration (indicated by dashed lines) to the collapsed configuration (indicated by arrows). To move the lower support $68_b$ between the expanded and collapsed configurations, the adjustment screw $50_b$ is first rotated in a clockwise manner until the locking member 216 secures the first elongated sleeve $34_b$ in place. After the first elongated sleeve $34_b$ is locked in place, an axial force (e.g., using tactile means) is applied to the first and second lever arms 238 and 240 of the actuating handle 210 (indicated by arrows). Application of the axial force causes the first end portion 246 of the second lever arm 240 to move longitudinally and thereby collapse the fingers 232 of the lower support $68_b$ so that the radial plane P of the lower support extends substantially perpendicular to the superior aspect 26 of the diseased mitral valve 22.

Figure 28:
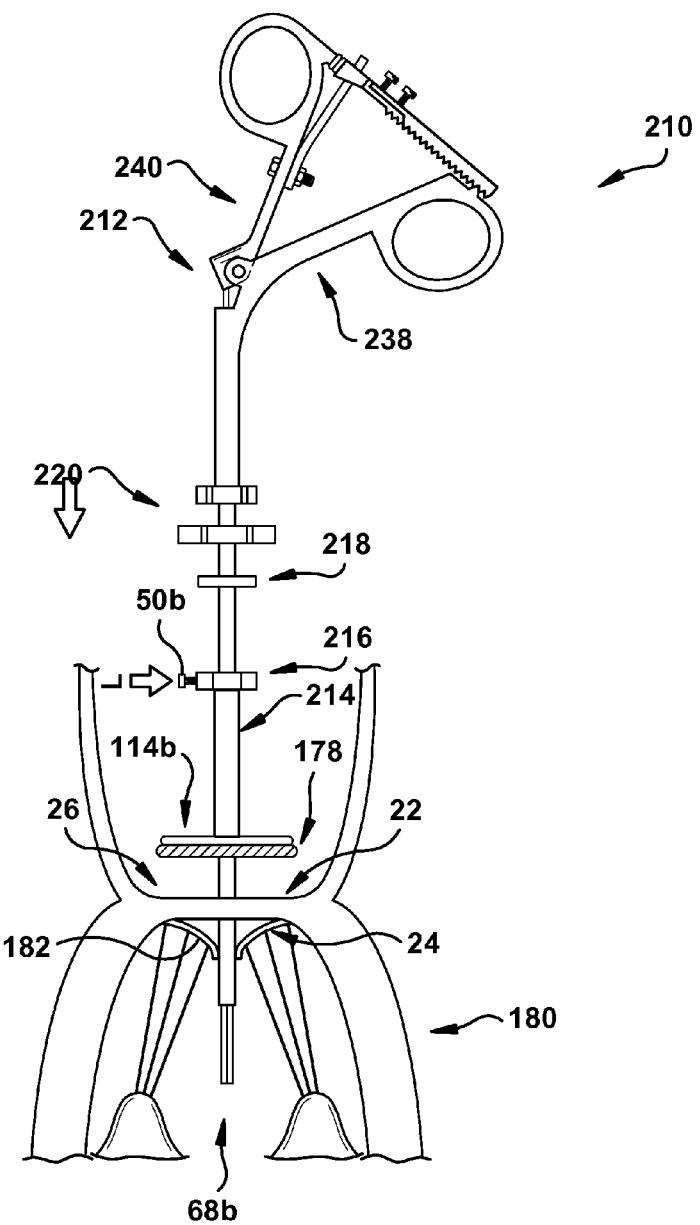
FIG. 28 is a side view showing the elongated shank of the apparatus in FIG. 27 being deployed through the diseased mitral valve.
Figure 29:
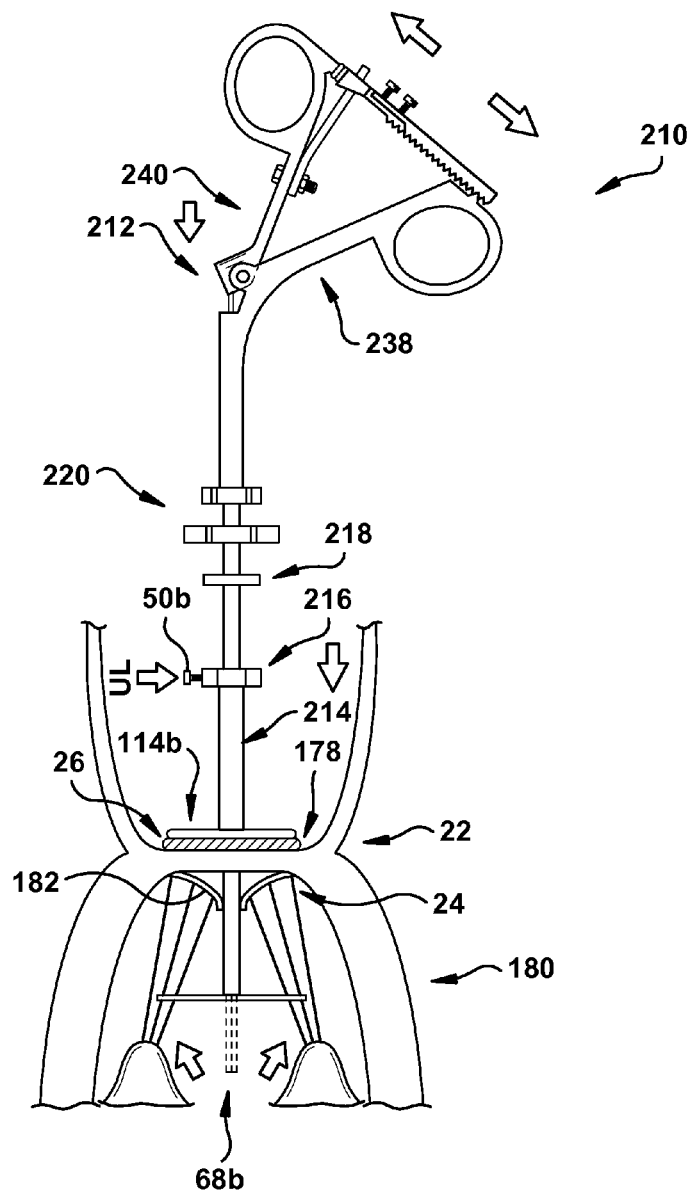
FIG. 29 is a side view showing the lower support in FIG. 28 in a deployed configuration.

After the lower support $68_b$ obtains the collapsed configuration, the lower support is extended through the diseased mitral valve 22 at Step 172, (FIG. 28). To ensure that the lower support 68b is properly oriented during advancement through the diseased mitral valve 22, the directional marker 218 and/or the rotation handle 220 can be adjusted as needed. Once the lower support $68_b$ is positioned below the diseased mitral valve 22 in the left ventricle 180, the lower support is moved into the expanded configuration by applying an axial force (e.g., using tactile means) to the first and second lever arms 238 and 240 of the actuating handle 210 (indicated by arrows) (FIG. 29). Application of the axial force causes the first end portion 246 of the second lever arm 240 to move longitudinally (i.e., towards the lower support $68_b$) and expand the fingers 232 of the lower support so that the radial plane P of the lower support extends substantially parallel to the superior aspect 26 of the diseased mitral valve 22.

Figure 30:
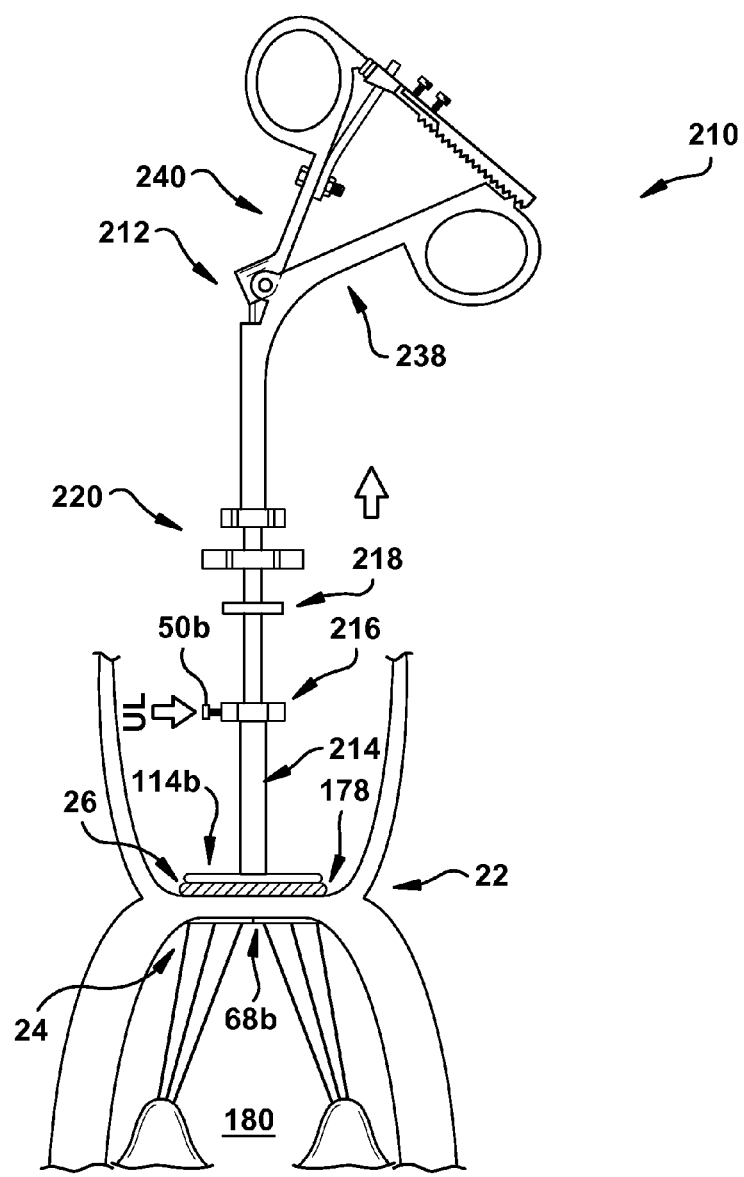
FIG. 30 is a side view showing the diseased cardiac valve in FIG. 29 being sandwiched between the lower support and the annuloplasty ring.

As shown in FIG. 29, the adjustment screw $50_b$ is rotated in a counter-clockwise manner to slidably release the first elongated sleeve $34_b$. Next, an axial force (e.g., using tactile means) is applied at the first end $38_b$ of the first elongated sleeve $34_b$ so that the first elongated sleeve moves towards the diseased mitral valve 22 and firmly contacts the superior aspect 26 of the mitral annulus. At Step $174_c$, an axial force (indicated by arrow) is then applied to the apparatus $10_b$ (e.g., at the first end portion $28_b$ of the elongated shank $12_b$ or the actuating handle 210) so that the lower support $68_b$ firmly contacts the inferior aspect 24 of the diseased mitral valve 22 and thereby sandwiches the mitral annulus between the annuloplasty ring 178 and the lower support (FIG. 30). Engagement of the lower support $68_b$ with the inferior aspect 24 of the mitral annulus stabilizes the cardiac tissue surrounding the diseased mitral valve 22 and facilitates delivery of the annuloplasty ring 178.

Once the mitral annulus is sandwiched between the annuloplasty ring 178 and the lower support $68_b$, the annuloplasty ring can be securely sutured in place about the mitral annulus at Step $176_c$. Implantation of the annuloplasty ring 178 remodels the mitral annulus so that the mitral leaflets 182 properly coapt and thereby mitigate or prevent regurgitation of blood through the mitral valve 22. Proper transvalvular blood flow can be assessed following implantation using one or more techniques known in the art, such as Doppler echocardiography.

Figure 31:
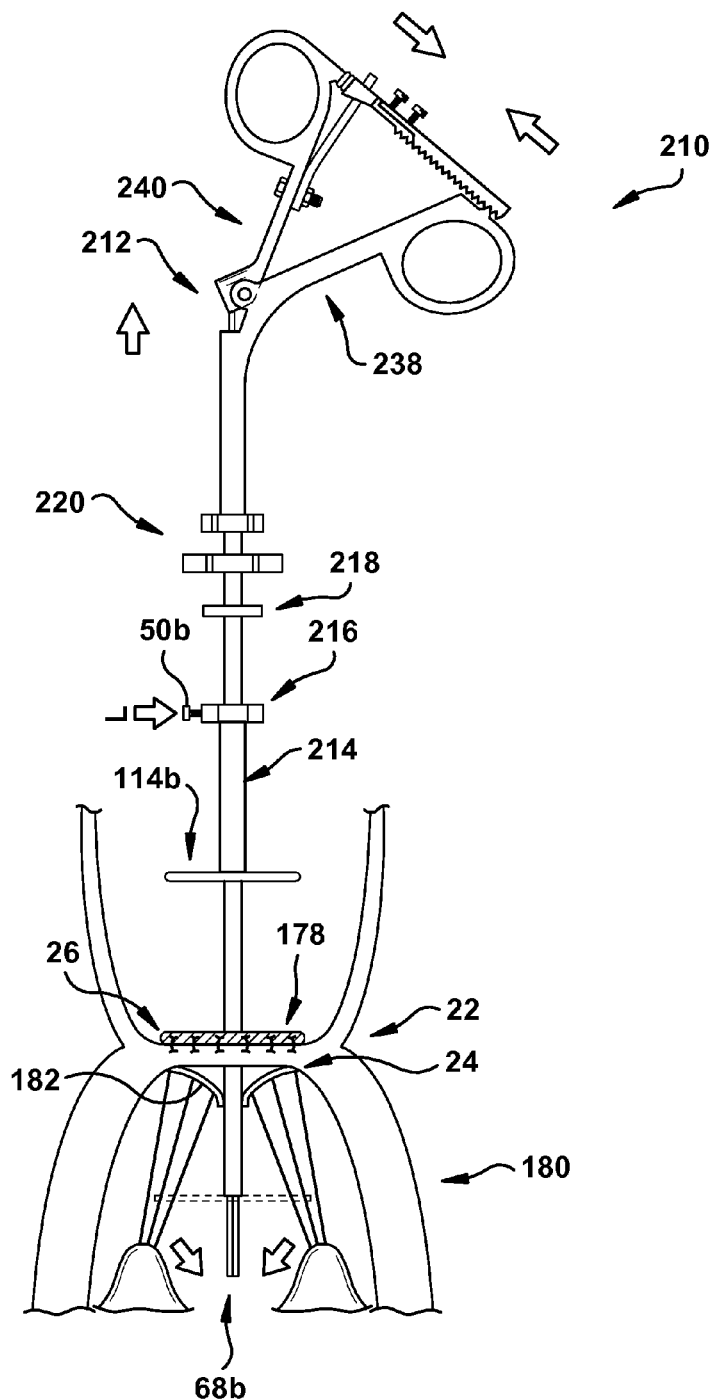
FIG. 31 is a side view showing the apparatus in FIG. 30 being withdrawn following implantation of the annuloplasty ring.

As shown in FIG. 31, the apparatus $10_b$ is removed following successful implantation of the annuloplasty ring 178. To remove the apparatus $10_b$, the adjustment screw $50_b$ is first rotated in a counter-clockwise manner. An axial force is then applied to the locking member 216 so that the first elongated sleeve $34_b$ slides over the second elongated sleeve $36_b$ towards the actuating handle 210. Next, the adjustment screw $50_b$ is locked and the elongated shank $12_b$ moved distally to disengage the lower support $68_b$ from the inferior aspect 24 of the diseased mitral valve 22. The lower support $68_b$ is then placed in the collapsed configuration (as described above). With the lower support $68_b$ in the collapsed configuration, the entire apparatus $10_b$ is completely removed and the operation concluded.

From the above description of the invention, those skilled in the art will perceive improvements, changes and modifications. For example, suction can be applied simultaneously through the vacuum ports 164 and 162 of the upper and lower supports 114, and $68_a$ prior to contact with the superior and inferior aspects 26 and 24 of the diseased cardiac valve 20 (respectively). Additionally, it will be appreciated that the apparatus $10_b$ can include a vacuum mechanism 140 similar to the one described above. Such improvements, changes, and modifications are within the skill of the art and are intended to be covered by the appended claims.

Having described the invention, we claim:

1. An apparatus for delivering an annuloplasty ring or prosthetic valve to a diseased cardiac valve having an inferior aspect and a superior aspect, said apparatus comprising:

an elongated shank having a first end portion, a second end portion, and a first longitudinal axis extending between said first and second end portions, said first end portion including a rotatable annular lower support for contacting the inferior aspect of the diseased cardiac valve and a fixing member for securing the annuloplasty ring or prosthetic valve to, or in place of, the diseased cardiac valve, said lower support comprising an annular ring having oppositely disposed upper and lower surfaces and a plane extending radially between said upper and lower surfaces, said lower support and said fixing member being movable relative to one another along said first longitudinal axis;

a brace member comprising a barrel portion operably connected to a drive system, said barrel portion including a first end portion, a second end portion, and a second longitudinal axis extending between said first and second end portions, said drive system comprising a housing operably connected to an actuating handle, said drive system for slidably extending and withdrawing said elongated shank along said second longitudinal axis, said first end portion of said barrel portion includes an annular upper support configured for receiving an annuloplasty ring or prosthetic heart valve; and a locking mechanism operably connected to said housing and said elongated shank, said locking mechanism for securing said lower support and said fixing member at separate points along said first longitudinal axis of said elongated shank.

2. The apparatus of claim 1, wherein said fixing member has an annular configuration.

3. The apparatus of claim 1 further comprising a vacuum mechanism for stabilizing at least a portion of the tissue surrounding the diseased cardiac valve, said vacuum mechanism being operably coupled to at least one of the upper support and the lower support.

4. The apparatus of claim 1, wherein said second end portion of said elongated shank includes a lower support adjustment mechanism for controlling said lower support.

5. The apparatus of claim 1, wherein each of said upper and lower supports have a saddle-shaped configuration.

6. A method for delivering an annuloplasty ring or prosthetic heart valve to a diseased cardiac valve having an inferior aspect and a superior aspect, said method comprising the steps of:

providing an apparatus comprising an elongated shank, a brace member, and a locking mechanism, the elongated shank having a first end portion, a second end portion, and a first longitudinal axis extending between the first and second end portions, the first end portion including a rotatable annular lower support and a fixing member, the lower support comprising an annular ring having oppositely disposed upper and lower surfaces and a plane extending radially between the upper and lower surfaces, the brace member comprising a barrel portion operably connected to a drive system, the barrel portion including a first end portion, a second end portion, and a second longitudinal axis extending between the first and second end portions, the drive system comprising a housing operably connected to an actuating handle, the locking mechanism being operably connected to the housing and the elongated shank;

providing one of an annuloplasty ring or a prosthetic valve on an annular upper support;

positioning the first end portion of the barrel portion about the superior aspect of the diseased cardiac valve;

extending the lower support through the diseased cardiac valve;

sandwiching at least a portion of the diseased cardiac valve between the upper and lower supports; and implanting the annuloplasty ring or prosthetic valve on, or in place of, the diseased cardiac valve.

7. The method of claim 6, wherein said step of extending the lower support through the diseased cardiac valve further comprises the steps of:

operating a lower support adjustment mechanism of the elongated shank so that the radial plane of the lower support extends substantially perpendicular to the superior aspect of the diseased cardiac valve;

operating the actuating handle so that the lower support is traversed through the diseased cardiac valve into the ventricle; and operating the lower support adjustment mechanism so that the radial plane of the lower support extends substantially parallel to the inferior aspect of the diseased cardiac valve.

8. The method of claim 6, wherein said step of sandwiching at least a portion of the diseased cardiac valve between the upper and lower supports further comprises the step of operating the actuating handle to withdraw the elongated shank so that the upper surface of the lower support contacts the inferior aspect of the diseased cardiac valve.

9. The method of claim 6, wherein said step of implanting the annuloplasty ring or prosthetic valve on, or in place of, the diseased cardiac valve further comprises the steps of:

operating the actuating handle so that the fixing member contacts an upper support of the brace member; and securing the annuloplasty ring or prosthetic valve to, or in place of, the diseased cardiac valve.

10. The method of claim 6, wherein said step of providing an apparatus further comprises providing a vacuum mechanism, the vacuum mechanism being operably connected to at least one of the upper and lower supports.

11. The method of claim 10 further comprising the step of applying a vacuum through at least one of the upper and lower supports to stabilize at least a portion of the heart tissue surrounding the diseased cardiac valve.

* * * * *